US011187572B2

(12) United States Patent
Fulkerson et al.

(10) Patent No.: US 11,187,572 B2
(45) Date of Patent: Nov. 30, 2021

(54) DIALYSIS SYSTEMS WITH A SUSPENDED RESERVOIR

(71) Applicant: Fresenius Medical Care Holdings, Inc., Waltham, MA (US)

(72) Inventors: Barry Neil Fulkerson, Longmont, CO (US); Joe Fazio, Santa Ana, CA (US); Alec Huang, Irvine, CA (US); Brian Thomas Kelly, Anaheim Hills, CA (US); Tam Nolan, Oceanside, CA (US); Mark Smith, Longmont, CO (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 67 days.

(21) Appl. No.: 16/711,240

(22) Filed: Dec. 11, 2019

(65) Prior Publication Data
US 2020/0191640 A1 Jun. 18, 2020

Related U.S. Application Data

(63) Continuation of application No. 15/808,189, filed on Nov. 9, 2017, now Pat. No. 10,539,450, which is a
(Continued)

(51) Int. Cl.
*G01G 17/04* (2006.01)
*G01G 19/14* (2006.01)
(Continued)

(52) U.S. Cl.
CPC ............ *G01G 17/04* (2013.01); *A61M 1/3621* (2013.01); *B01D 61/30* (2013.01); *G01G 3/15* (2013.01);
(Continued)

(58) Field of Classification Search
CPC .......... G01G 17/04; G01G 21/28; G01G 3/15; G01G 19/14; A61M 1/3621;
(Continued)

(56) References Cited

U.S. PATENT DOCUMENTS 2,276,843 A 3/1942 Hathaway
2,328,381 A 8/1943 Jaffe
(Continued)

FOREIGN PATENT DOCUMENTS

AU 2017203445 B2 8/2019
CN 2183771 Y 11/1994
(Continued)

OTHER PUBLICATIONS

Timby et al., Introductory Medical-Surgical Nursing, Lippincott Williams Wilkins, Ninth Edition, Chapter 28, p. 433.
(Continued)

*Primary Examiner* — Randy W Gibson
(74) *Attorney, Agent, or Firm* — Novel IP

(57) ABSTRACT

A load suspension and weighing system for a removable reservoir unit of a portable dialysis machine includes a centrally located flexure assembly. The flexure assembly includes magnets and a number of flexure rings which allow for movement of the magnets about a fixed circuit board. Sensors in the circuit board sense changes in the magnetic field as the magnets move in relation to the circuit board. The magnetic field changes produce a voltage output which is used by a processor to generate weight calculations. The top of the flexure assembly is attached to the interior of the dialysis machine. The entirety of the reservoir unit is suspended by a first internal frame that is attached to the bottom of the flexure assembly. Having a single flexure assembly positioned above the reservoir unit provides more accurate
(Continued)

weight measurements while also preventing damage to the assembly from water spillage.

20 Claims, 13 Drawing Sheets

Related U.S. Application Data continuation of application No. 14/848,012, filed on Sep. 8, 2015, now Pat. No. 9,841,310, which is a continuation of application No. 13/726,450, filed on Dec. 24, 2012, now Pat. No. 9,157,786.

(51) Int. Cl.
  *G01G 3/15* (2006.01)
  *A61M 1/36* (2006.01)
  *B01D 61/30* (2006.01)
  *G01L 1/04* (2006.01)
(52) U.S. Cl.
  CPC ..... *G01G 19/14* (2013.01); *A61M 2205/3393* (2013.01); *G01L 1/04* (2013.01); *G01L 1/044* (2013.01); *G01L 1/046* (2013.01)
(58) Field of Classification Search
  CPC .. A61M 2205/3393; B01D 61/30; G01L 1/04; G01L 1/044; G01L 1/046
  See application file for complete search history.

(56) References Cited

U.S. PATENT DOCUMENTS

| | | |
|---|---|---|
| 2,569,105 A | 9/1951 | James |
| 2,720,879 A | 10/1955 | Albin |
| 2,977,791 A | 4/1961 | Dubsky |
| 3,200,591 A | 8/1965 | Ray |
| 3,216,281 A | 11/1965 | Teichert |
| 3,242,456 A | 3/1966 | Duncan |
| 3,308,798 A | 3/1967 | Snider |
| 3,384,424 A | 5/1968 | Raines |
| 3,388,803 A | 6/1968 | Scott |
| 3,416,664 A | 12/1968 | Kumme |
| 3,420,492 A | 1/1969 | Ray |
| 3,464,448 A | 9/1969 | Schmitz |
| 3,511,469 A | 5/1970 | Bell |
| 3,514,674 A | 5/1970 | Toshio |
| 3,597,124 A | 8/1971 | Adams |
| 3,669,878 A | 6/1972 | Marantz |
| 3,669,880 A | 6/1972 | Marantz |
| 3,703,959 A | 11/1972 | Raymond |
| 3,709,222 A | 1/1973 | De Vries |
| 3,728,654 A | 4/1973 | Tada |
| 3,746,175 A | 7/1973 | Markley |
| 3,752,189 A | 8/1973 | Marr |
| 3,803,913 A | 4/1974 | Tracer |
| 3,814,376 A | 6/1974 | Reinicke |
| 3,841,799 A | 10/1974 | Spinosa |
| 3,850,835 A | 11/1974 | Marantz |
| 3,872,863 A | 3/1975 | Lasker |
| 3,884,808 A | 5/1975 | Scott |
| 3,894,431 A | 7/1975 | Muston |
| 3,902,490 A | 9/1975 | Jacobsen |
| 3,918,037 A | 11/1975 | Hall |
| 3,927,955 A | 12/1975 | Spinosa |
| 3,946,731 A | 3/1976 | Lichtenstein |
| 3,961,918 A | 6/1976 | Johnson |
| 3,983,361 A | 9/1976 | Wild |
| 3,989,622 A | 11/1976 | Marantz |
| 3,989,625 A | 11/1976 | Mason |
| 3,994,799 A | 11/1976 | Yao |
| 4,000,072 A | 12/1976 | Sato |
| 4,047,099 A | 9/1977 | Berger |
| 4,071,444 A | 1/1978 | Ash |
| 4,079,007 A | 3/1978 | Hutchisson |
| 4,083,770 A | 4/1978 | Deering |
| 4,083,777 A | 4/1978 | Hutchisson |
| 4,094,775 A | 6/1978 | Mueller |
| 4,099,700 A | 7/1978 | Young |
| 4,113,614 A | 9/1978 | Rollo |
| 4,118,314 A | 10/1978 | Yoshida |
| 4,155,852 A | 5/1979 | Fischel |
| 4,159,748 A | 7/1979 | Staudinger |
| 4,187,057 A | 2/1980 | Xanthopoulos |
| 4,209,392 A | 6/1980 | Wallace |
| 4,212,738 A | 7/1980 | Henne |
| 4,247,393 A | 1/1981 | Wallace |
| 4,253,493 A | 3/1981 | English |
| 4,259,985 A | 4/1981 | Bergmann |
| 4,267,040 A | 5/1981 | Schael |
| 4,269,708 A | 5/1981 | Bonomini |
| 4,326,955 A | 4/1982 | Babb |
| 4,348,283 A | 9/1982 | Ash |
| 4,354,562 A | 10/1982 | Newman |
| 4,368,737 A | 1/1983 | Ash |
| 4,371,072 A | 2/1983 | Voegeli |
| 4,371,385 A | 2/1983 | Johnson |
| 4,381,999 A | 5/1983 | Boucher |
| 4,387,777 A | 6/1983 | Ash |
| 4,390,073 A | 6/1983 | Rosen |
| 4,397,189 A | 8/1983 | Johnson |
| 4,397,519 A | 8/1983 | Cooney |
| 4,402,694 A | 9/1983 | Ash |
| 4,403,765 A | 9/1983 | Fisher |
| 4,403,984 A | 9/1983 | Ash |
| 4,413,988 A | 11/1983 | Handt |
| 4,430,098 A | 2/1984 | Bowman |
| 4,436,620 A | 3/1984 | Bellotti |
| 4,443,333 A | 4/1984 | Mahurkar |
| 4,460,555 A | 7/1984 | Thompson |
| 4,464,172 A | 8/1984 | Lichtenstein |
| 4,466,804 A | 8/1984 | Hino |
| 4,469,593 A | 9/1984 | Ishihara |
| 4,477,342 A | 10/1984 | Allan |
| 4,480,483 A | 11/1984 | McShane |
| 4,498,902 A | 2/1985 | Ash |
| 4,531,799 A | 7/1985 | Gray |
| 4,535,637 A | 8/1985 | Feller |
| 4,559,039 A | 12/1985 | Ash |
| 4,563,170 A | 1/1986 | Aigner |
| 4,581,141 A | 4/1986 | Ash |
| 4,586,576 A | 5/1986 | Inoue |
| 4,596,550 A | 6/1986 | Troutner |
| 4,599,055 A | 7/1986 | Dykstra |
| 4,606,826 A | 8/1986 | Sano |
| 4,630,799 A | 12/1986 | Nolan |
| 4,650,587 A | 3/1987 | Polak |
| 4,661,246 A | 4/1987 | Ash |
| 4,666,598 A | 5/1987 | Heath |
| 4,680,122 A | 7/1987 | Barone |
| 4,683,053 A | 7/1987 | Polaschegg |
| 4,710,164 A | 12/1987 | Levin |
| 4,731,072 A | 3/1988 | Aid |
| 4,740,755 A | 4/1988 | Ogawa |
| 4,750,705 A | 6/1988 | Zippe |
| 4,762,618 A | 8/1988 | Gummesson |
| 4,765,421 A | 8/1988 | Newton |
| 4,765,907 A | 8/1988 | Scott |
| 4,777,953 A | 10/1988 | Ash |
| 4,802,540 A | 2/1989 | Grabovac |
| 4,806,247 A | 2/1989 | Schoendorfer |
| 4,808,089 A | 2/1989 | Buchholtz |
| 4,815,547 A | 3/1989 | Dillon |
| 4,823,597 A | 4/1989 | White |
| 4,826,663 A | 5/1989 | Alberti |
| 4,828,543 A | 5/1989 | Weiss |
| 4,828,693 A | 5/1989 | Lindsay |
| 4,831,884 A | 5/1989 | Drenthen |
| 4,840,542 A | 6/1989 | Abbott |
| 4,854,322 A | 8/1989 | Ash |
| 4,861,242 A | 8/1989 | Finsterwald |
| 4,881,839 A | 11/1989 | Grimm |
| 4,882,937 A | 11/1989 | Leon |
| 4,885,942 A | 12/1989 | Magori |

(56) References Cited

U.S. PATENT DOCUMENTS

| | | | | |
|---|---|---|---|---|
| 4,894,164 | A | 1/1990 | Polaschegg | |
| 4,897,189 | A | 1/1990 | Greenwood | |
| 4,909,713 | A | 3/1990 | Finsterwald | |
| 4,914,819 | A | 4/1990 | Ash | |
| 4,931,777 | A | 6/1990 | Chiang | |
| 4,943,279 | A | 7/1990 | Samiotes | |
| 4,950,244 | A | 8/1990 | Fellingham | |
| 4,950,395 | A | 8/1990 | Richalley | |
| 4,968,422 | A | 11/1990 | Runge | |
| 4,985,015 | A | 1/1991 | Obermann | |
| 4,990,258 | A | 2/1991 | Bjare | |
| 4,994,035 | A | 2/1991 | Mokros | |
| 4,995,268 | A | 2/1991 | Ash | |
| 4,997,570 | A | 3/1991 | Polaschegg | |
| 5,000,274 | A | 3/1991 | Bullivant | |
| 5,002,054 | A | 3/1991 | Ash | |
| 5,009,101 | A | 4/1991 | Branam | |
| 5,011,607 | A | 4/1991 | Shinzato | |
| 5,024,586 | A | 6/1991 | Meiri | |
| 5,032,261 | A | 7/1991 | Pyper | |
| 5,074,368 | A | 12/1991 | Bullivant | |
| 5,100,554 | A | 3/1992 | Polaschegg | |
| 5,114,580 | A | 5/1992 | Ahmad | |
| 5,138,138 | A | 8/1992 | Theilacker | |
| 5,147,613 | A | 9/1992 | Heilmann | |
| 5,149,318 | A * | 9/1992 | Lindsay | A61M 1/3627 128/DIG. 3 |
| 5,152,174 | A | 10/1992 | Labudde | |
| 5,157,332 | A | 10/1992 | Reese | |
| 5,161,779 | A | 11/1992 | Graner | |
| 5,170,789 | A | 12/1992 | Narayan | |
| 5,188,604 | A | 2/1993 | Orth | |
| 5,198,335 | A | 3/1993 | Sekikawa | |
| 5,211,643 | A | 5/1993 | Reinhardt | |
| 5,215,450 | A | 6/1993 | Tamari | |
| 5,220,843 | A | 6/1993 | Rak | |
| 5,228,308 | A | 7/1993 | Day | |
| 5,230,341 | A | 7/1993 | Polaschegg | |
| 5,230,614 | A | 7/1993 | Zanger | |
| 5,254,080 | A * | 10/1993 | Lindsay | A61M 1/3627 128/DIG. 3 |
| 5,258,127 | A | 11/1993 | Gsell | |
| 5,259,961 | A | 11/1993 | Eigendorf | |
| 5,277,820 | A | 1/1994 | Ash | |
| 5,284,470 | A | 2/1994 | Beltz | |
| 5,284,559 | A | 2/1994 | Lim | |
| 5,295,505 | A | 3/1994 | Polaschegg | |
| 5,304,114 | A | 4/1994 | Cosman | |
| 5,304,349 | A | 4/1994 | Polaschegg | |
| 5,308,315 | A | 5/1994 | Khuri | |
| 5,322,258 | A | 6/1994 | Bosch | |
| 5,322,519 | A | 6/1994 | Ash | |
| 5,336,165 | A | 8/1994 | Twardowski | |
| 5,339,699 | A | 8/1994 | Carignan | |
| 5,346,472 | A | 9/1994 | Keshaviah | |
| 5,347,115 | A | 9/1994 | Sherman | |
| 5,352,364 | A | 10/1994 | Kruger | |
| 5,360,445 | A | 11/1994 | Goldowsky | |
| 5,385,005 | A | 1/1995 | Ash | |
| D355,816 | S | 2/1995 | Ash | |
| 5,391,143 | A | 2/1995 | Kensey | |
| 5,405,315 | A | 4/1995 | Khuri | |
| 5,405,320 | A | 4/1995 | Twardowski | |
| 5,408,576 | A | 4/1995 | Bishop | |
| 5,415,532 | A | 5/1995 | Loughnane | |
| 5,441,636 | A | 8/1995 | Chevallet | |
| 5,445,630 | A | 8/1995 | Richmond | |
| 5,460,493 | A | 10/1995 | Deniega | |
| 5,468,388 | A | 11/1995 | Goddard | |
| 5,469,737 | A | 11/1995 | Smith | |
| 5,476,444 | A | 12/1995 | Keeling | |
| 5,514,335 | A * | 5/1996 | Leonard | B01D 63/02 422/46 |
| 5,518,015 | A | 5/1996 | Berget | |
| D370,531 | S | 6/1996 | Ash | |
| 5,536,412 | A | 7/1996 | Ash | |
| 5,540,265 | A | 7/1996 | Polaschegg | |
| 5,545,131 | A | 8/1996 | Davankov | |
| 5,577,891 | A | 11/1996 | Loughnane | |
| 5,580,460 | A | 12/1996 | Polaschegg | |
| 5,580,522 | A * | 12/1996 | Leonard | B01D 63/02 422/46 |
| 5,586,665 | A * | 12/1996 | Brousseau | A47F 7/285 193/12 |
| 5,591,344 | A | 1/1997 | Kenley | |
| 5,609,770 | A | 3/1997 | Zimmerman | |
| 5,614,677 | A | 3/1997 | Wamsiedler | |
| 5,629,871 | A | 3/1997 | Love | |
| 5,616,305 | A | 4/1997 | Mathieu | |
| 5,624,551 | A | 4/1997 | Baumann | |
| 5,624,572 | A | 4/1997 | Larson | |
| 5,632,897 | A | 5/1997 | Mathieu | |
| 5,644,285 | A | 7/1997 | Maurer | |
| 5,647,853 | A | 7/1997 | Feldmann | |
| 5,650,704 | A | 7/1997 | Pratt | |
| 5,674,390 | A | 10/1997 | Matthews | |
| 5,679,245 | A | 10/1997 | Manica | |
| 5,685,835 | A | 11/1997 | Brugger | |
| 5,690,821 | A | 11/1997 | Kenley | |
| 5,693,008 | A | 12/1997 | Brugger | |
| 5,695,473 | A | 12/1997 | Olsen | |
| 5,698,083 | A | 12/1997 | Glass | |
| 5,711,883 | A | 1/1998 | Folden | |
| 5,713,850 | A | 2/1998 | Heilmann | |
| 5,725,773 | A | 3/1998 | Polaschegg | |
| 5,725,776 | A | 3/1998 | Kenley | |
| 5,744,027 | A | 4/1998 | Connell | |
| 5,753,173 | A * | 5/1998 | Leonard | A61M 1/3627 264/503 |
| 5,760,313 | A | 6/1998 | Guentner | |
| 5,762,782 | A | 6/1998 | Kenley | |
| 5,765,591 | A | 6/1998 | Wasson | |
| 5,770,806 | A | 6/1998 | Hiismaeki | |
| 5,782,796 | A | 7/1998 | Din | |
| 5,788,099 | A | 8/1998 | Treu | |
| 5,794,669 | A | 8/1998 | Polaschegg | |
| 5,840,068 | A | 11/1998 | Cartledge | |
| 5,858,186 | A | 1/1999 | Glass | |
| 5,876,419 | A | 3/1999 | Carpenter | |
| 5,902,336 | A | 5/1999 | Mishkin | |
| 5,906,978 | A | 5/1999 | Ash | |
| 5,919,369 | A | 7/1999 | Ash | |
| 5,928,177 | A | 7/1999 | Brugger | |
| 5,938,938 | A | 8/1999 | Bosetto | |
| 5,944,684 | A | 8/1999 | Roberts | |
| 5,945,343 | A | 8/1999 | Munkholm | |
| 5,947,953 | A | 9/1999 | Ash | |
| 5,951,870 | A | 9/1999 | Utterberg | |
| 5,980,481 | A | 11/1999 | Gorsuch | |
| 5,984,891 | A | 11/1999 | Keilman | |
| 5,989,423 | A | 11/1999 | Kamen | |
| 5,989,438 | A | 11/1999 | Fumiyama | |
| 6,012,342 | A | 1/2000 | Blight | |
| 6,042,561 | A | 3/2000 | Ash | |
| 6,044,691 | A | 4/2000 | Kenley | |
| 6,047,108 | A | 4/2000 | Sword | |
| 6,062,256 | A | 5/2000 | Miller | |
| 6,069,343 | A | 5/2000 | Kolowich | |
| 6,086,753 | A | 7/2000 | Ericson | |
| 6,113,554 | A | 9/2000 | Gilcher | |
| 6,116,269 | A | 9/2000 | Maxson | |
| 6,117,100 | A | 9/2000 | Powers | |
| 6,117,122 | A | 9/2000 | Din | |
| 6,118,082 | A | 9/2000 | Bissette | |
| 6,121,555 | A | 9/2000 | Nowosielski | |
| 6,156,007 | A | 12/2000 | Ash | |
| 6,168,578 | B1 | 1/2001 | Diamond | |
| 6,187,199 | B1 | 2/2001 | Goldau | |
| 6,190,349 | B1 | 2/2001 | Ash | |
| 6,196,922 | B1 | 3/2001 | Hantschk | |
| 6,196,992 | B1 | 3/2001 | Keilman | |
| 6,200,485 | B1 | 3/2001 | Kitaevich | |
| 6,217,540 | B1 | 4/2001 | Yazawa | |
| 6,228,047 | B1 | 5/2001 | Dadson | |

(56) References Cited

U.S. PATENT DOCUMENTS

| | | |
|---|---|---|
| 6,234,989 B1 | 5/2001 | Brierton |
| 6,240,789 B1 | 6/2001 | Morlan |
| 6,254,567 B1 | 7/2001 | Treu |
| 6,264,611 B1 | 7/2001 | Ishikawa |
| 6,264,680 B1 | 7/2001 | Ash |
| 6,280,406 B1 | 8/2001 | Dolcek |
| 6,284,131 B1 | 9/2001 | Hogard |
| 6,287,516 B1 | 9/2001 | Matson |
| 6,289,749 B1 | 9/2001 | Sanders |
| 6,303,036 B1 | 10/2001 | Collins |
| 6,325,774 B1 | 12/2001 | Bene |
| 6,332,985 B1 | 12/2001 | Sherman |
| 6,341,758 B1 | 1/2002 | Shih |
| 6,348,162 B1 | 2/2002 | Ash |
| 6,354,565 B1 | 3/2002 | Doust |
| 6,406,631 B1 | 6/2002 | Collins |
| 6,409,699 B1 | 6/2002 | Ash |
| 6,416,293 B1 | 7/2002 | Bouchard |
| 6,468,427 B1 | 10/2002 | Frey |
| 6,471,872 B2 | 10/2002 | Kitaevich |
| 6,487,904 B1 | 12/2002 | Myhre |
| 6,491,656 B1 | 12/2002 | Morris |
| 6,491,673 B1 | 12/2002 | Palumbo |
| 6,497,675 B1 | 12/2002 | Davankov |
| 6,517,044 B1 | 2/2003 | Lin |
| 6,517,045 B1 | 2/2003 | Northedge |
| 6,551,513 B2 | 4/2003 | Nikaido |
| 6,554,789 B1 | 4/2003 | Brugger |
| 6,561,997 B1 | 5/2003 | Weitzel |
| 6,565,395 B1 | 5/2003 | Schwarz |
| 6,572,576 B2 | 6/2003 | Brugger |
| 6,572,641 B2 | 6/2003 | Brugger |
| 6,579,253 B1 | 6/2003 | Burbank |
| 6,579,460 B1 | 6/2003 | Willis |
| 6,582,385 B2 | 6/2003 | Burbank |
| 6,589,482 B1 | 7/2003 | Burbank |
| 6,595,943 B1 | 7/2003 | Burbank |
| 6,607,495 B1 | 8/2003 | Skalak |
| 6,610,036 B2 | 8/2003 | Branch |
| 6,623,470 B2 | 9/2003 | Munis |
| 6,627,164 B1 | 9/2003 | Wong |
| 6,632,192 B2 | 10/2003 | Gorsuch |
| 6,638,477 B1 | 10/2003 | Treu |
| 6,638,478 B1 | 10/2003 | Treu |
| 6,649,063 B2 | 11/2003 | Brugger |
| 6,653,841 B1 | 11/2003 | Koerdt |
| 6,673,314 B1 | 1/2004 | Burbank |
| 6,681,624 B2 | 1/2004 | Furuki |
| 6,685,664 B2 | 2/2004 | Levin |
| 6,690,280 B2 | 2/2004 | Citrenbaum |
| 6,695,803 B1 | 2/2004 | Robinson |
| 6,702,561 B2 | 3/2004 | Stillig |
| 6,706,007 B2 | 3/2004 | Gelfand |
| 6,730,266 B2 | 5/2004 | Matson |
| 6,743,193 B2 | 6/2004 | Brugger |
| 6,752,172 B2 | 6/2004 | Lauer |
| 6,758,975 B2 | 7/2004 | Peabody |
| 6,764,460 B2 | 7/2004 | Dolecek |
| 6,773,412 B2 | 8/2004 | OMahony |
| 6,776,912 B2 | 8/2004 | Baurmeister |
| 6,796,955 B2 | 9/2004 | OMahony |
| 6,818,196 B2 | 11/2004 | Wong |
| 6,830,553 B1 | 12/2004 | Burbank |
| 6,836,201 B1 | 12/2004 | Devenyi |
| 6,841,172 B1 | 1/2005 | Ash |
| 6,843,779 B1 | 1/2005 | Andrysiak |
| 6,852,090 B2 | 2/2005 | Burbank |
| 6,872,346 B2 | 3/2005 | Stillig |
| 6,878,283 B2 | 4/2005 | Thompson |
| 6,886,801 B2 | 5/2005 | Hallback |
| 6,890,315 B1 | 5/2005 | Levin |
| 6,899,691 B2 | 5/2005 | Bainbridge |
| 6,923,782 B2 | 8/2005 | Omahony |
| 6,948,697 B2 | 9/2005 | Herbert |
| 6,955,655 B2 | 10/2005 | Burbank |
| 6,958,049 B1 | 10/2005 | Ash |
| 6,960,179 B2 | 11/2005 | Gura |
| 6,960,328 B2 | 11/2005 | Bortun |
| 6,979,309 B2 | 12/2005 | Burbank |
| 7,004,924 B1 | 2/2006 | Brugger |
| 7,007,549 B2 | 3/2006 | Kwon |
| 7,033,498 B2 | 4/2006 | Wong |
| 7,037,428 B1 | 5/2006 | Robinson |
| 7,040,142 B2 | 5/2006 | Burbank |
| 7,059,195 B1 | 6/2006 | Liu |
| 7,087,026 B2 | 8/2006 | Callister |
| 7,087,033 B2 | 8/2006 | Brugger |
| 7,097,148 B2 | 8/2006 | DeWall |
| 7,101,519 B2 | 9/2006 | Wong |
| 7,112,273 B2 | 9/2006 | Weigel |
| 7,115,095 B2 | 10/2006 | Egler |
| 7,135,156 B2 | 11/2006 | Hai |
| 7,144,386 B2 | 12/2006 | Korkor |
| 7,146,861 B1 | 12/2006 | Cook |
| 7,147,613 B2 | 12/2006 | Burbank |
| 7,169,303 B2 | 1/2007 | Sullivan |
| 7,175,809 B2 | 2/2007 | Gelfand |
| 7,214,312 B2 | 5/2007 | Brugger |
| 7,226,538 B2 | 6/2007 | Brugger |
| 7,241,272 B2 | 7/2007 | Karoor |
| 7,252,767 B2 | 8/2007 | Bortun |
| 7,267,658 B2 | 9/2007 | Treu |
| 7,270,015 B1 | 9/2007 | Feller |
| 7,273,465 B2 | 9/2007 | Ash |
| 7,276,042 B2 | 10/2007 | Polaschegg |
| 7,300,413 B2 | 11/2007 | Burbank |
| 7,309,323 B2 | 12/2007 | Gura |
| 7,314,208 B1 | 1/2008 | Rightley |
| 7,317,967 B2 | 1/2008 | DiGianfilippo |
| 7,332,096 B2 | 2/2008 | Blickhan |
| 7,337,674 B2 | 3/2008 | Burbank |
| 7,338,460 B2 | 3/2008 | Burbank |
| 7,347,849 B2 | 3/2008 | Brugger |
| 7,351,218 B2 | 4/2008 | Bene |
| 7,387,022 B1 | 6/2008 | Korniyenko |
| 7,494,590 B2 | 2/2009 | Felding |
| 7,531,098 B2 | 5/2009 | Robinson |
| 7,566,432 B2 | 7/2009 | Wong |
| 7,597,677 B2 | 10/2009 | Gura |
| 7,605,710 B2 | 10/2009 | Crnkovich |
| 7,618,531 B2 | 11/2009 | Sugioka |
| 7,628,378 B2 | 12/2009 | Adams |
| 7,645,253 B2 | 1/2010 | Gura |
| 7,648,476 B2 | 1/2010 | Bock |
| 7,696,762 B2 | 4/2010 | Quackenbush |
| 7,713,226 B2 | 5/2010 | Ash |
| 7,736,507 B2 | 6/2010 | Wong |
| 7,755,488 B2 | 7/2010 | Dvorsky |
| 7,766,873 B2 | 8/2010 | Moberg |
| 7,776,210 B2 | 8/2010 | Rosenbaum |
| 7,780,619 B2 | 8/2010 | Brugger |
| 7,794,141 B2 | 9/2010 | Perry |
| 7,861,740 B2 | 1/2011 | Phallen |
| 7,873,489 B2 | 1/2011 | Dolgos |
| 7,874,999 B2 | 1/2011 | Busby |
| 7,886,611 B2 | 2/2011 | OMahony |
| 7,896,829 B2 | 3/2011 | Gura |
| 7,901,376 B2 | 3/2011 | Steck |
| 7,914,477 B2 | 3/2011 | Briggs |
| 7,922,898 B2 | 4/2011 | Jonsson |
| 7,922,899 B2 | 4/2011 | Vasta |
| 7,935,074 B2 | 5/2011 | Plahey |
| 7,959,129 B2 | 6/2011 | Matsumoto |
| 7,981,082 B2 | 7/2011 | Wang |
| 7,981,280 B2 | 7/2011 | Carr |
| 7,995,816 B2 | 8/2011 | Roger |
| 7,998,101 B2 | 8/2011 | Ash |
| 8,021,319 B2 | 9/2011 | Delnevo |
| 8,029,454 B2 | 10/2011 | Kelly |
| 8,034,161 B2 | 10/2011 | Gura |
| 8,034,235 B2 | 10/2011 | Rohde |
| 8,062,513 B2 | 11/2011 | Yu |
| 8,066,658 B2 | 11/2011 | Karoor |
| 8,070,707 B2 | 12/2011 | Gelfand |

(56) References Cited

U.S. PATENT DOCUMENTS

| | | | |
|---|---|---|---|
| 8,075,509 B2 | 12/2011 | Molducci |
| 8,078,333 B2 | 12/2011 | Kienman |
| 8,083,677 B2 | 12/2011 | Rohde |
| 8,105,260 B2 | 1/2012 | Tonelli |
| 8,105,487 B2 | 1/2012 | Fulkerson |
| 8,114,288 B2 | 2/2012 | Robinson |
| 8,118,276 B2 | 2/2012 | Sanders |
| 8,123,947 B2 | 2/2012 | Rohde |
| 8,152,751 B2 | 2/2012 | Roger |
| 8,142,383 B2 | 3/2012 | Dannenmaier |
| 8,187,184 B2 | 5/2012 | Muller |
| 8,192,401 B2 | 6/2012 | Morris |
| 8,197,431 B2 | 6/2012 | Bennison |
| 8,206,338 B2 | 6/2012 | Childers |
| 8,210,493 B2 | 7/2012 | Miyagawa |
| 8,221,320 B2 | 7/2012 | Bouton |
| 8,240,636 B2 | 8/2012 | Smith |
| 8,273,049 B2 | 9/2012 | Demers |
| 8,316,725 B2 | 11/2012 | Wade |
| 8,323,492 B2 | 12/2012 | Childers |
| 8,342,478 B1 | 1/2013 | Cordray |
| 8,376,978 B2 | 2/2013 | Roger |
| 8,393,690 B2 | 3/2013 | Grant |
| 8,449,487 B2 | 5/2013 | Hovland |
| 8,491,184 B2 | 7/2013 | Kamen |
| 8,597,505 B2 | 12/2013 | Fulkerson |
| 8,622,365 B2 | 1/2014 | Fukano |
| 8,696,626 B2 | 4/2014 | Kirsch |
| 9,308,307 B2 | 4/2016 | Fulkerson |
| 9,354,640 B2 | 5/2016 | Byler |
| 9,358,331 B2* | 6/2016 | Fulkerson | A61M 1/3458 |
| 9,360,129 B2 | 6/2016 | Smith |
| 9,517,296 B2 | 12/2016 | Fulkerson |
| 10,001,402 B1* | 6/2018 | Gyori | G01G 21/22 |
| 10,019,020 B2 | 7/2018 | Byler |
| 10,034,973 B2 | 7/2018 | Robinson |
| 10,064,502 B1* | 9/2018 | Gyori | H04W 4/80 |
| 10,258,731 B2 | 4/2019 | Fulkerson |
| 2001/0038083 A1 | 11/2001 | Sakurai |
| 2002/0050412 A1 | 5/2002 | Emery |
| 2002/0068364 A1 | 6/2002 | Arai |
| 2002/0085951 A1 | 7/2002 | Gelfand |
| 2002/0112609 A1 | 8/2002 | Wong |
| 2002/0113016 A1 | 8/2002 | Takai |
| 2002/0139419 A1 | 10/2002 | Flinchbaugh |
| 2002/0147423 A1 | 10/2002 | Burbank |
| 2002/0158019 A1 | 10/2002 | Collins |
| 2002/0187069 A1 | 12/2002 | Levin |
| 2002/0193679 A1 | 12/2002 | Malave |
| 2003/0001590 A1 | 1/2003 | Mengle |
| 2003/0012905 A1 | 1/2003 | Zumbrum |
| 2003/0042181 A1 | 3/2003 | Metzner |
| 2003/0048185 A1 | 3/2003 | Citrenbaum |
| 2003/0056585 A1 | 3/2003 | Furuki |
| 2003/0113931 A1 | 6/2003 | Pan |
| 2003/0113932 A1 | 6/2003 | Sternberg |
| 2003/0128125 A1 | 7/2003 | Burbank |
| 2003/0216677 A1 | 11/2003 | Pan |
| 2003/0220598 A1 | 11/2003 | Busby |
| 2003/0220606 A1 | 11/2003 | Busby |
| 2003/0230957 A1* | 12/2003 | Doerfler | A47B 43/02 312/257.1 |
| 2003/0236482 A1 | 12/2003 | Gorsuch |
| 2004/0018100 A1 | 1/2004 | Takagi |
| 2004/0019312 A1 | 1/2004 | Childers |
| 2004/0021108 A1 | 2/2004 | Hallback |
| 2004/0031756 A1 | 2/2004 | Suzuki |
| 2004/0167465 A1 | 8/2004 | Mihai |
| 2004/0195055 A1 | 10/2004 | Gilles |
| 2005/0006296 A1 | 1/2005 | Sullivan |
| 2005/0010190 A1 | 1/2005 | Yeakley |
| 2005/0045548 A1 | 3/2005 | Brugger |
| 2005/0070837 A1 | 3/2005 | Ferrarini |
| 2005/0086008 A1 | 4/2005 | Digianfilippo |
| 2005/0092079 A1 | 5/2005 | Ales |
| 2005/0101901 A1 | 5/2005 | Gura |
| 2005/0113734 A1 | 5/2005 | Brugger |
| 2005/0131332 A1 | 6/2005 | Kelly |
| 2005/0133439 A1 | 6/2005 | Blickhan |
| 2005/0150309 A1 | 7/2005 | Beard |
| 2005/0209547 A1 | 9/2005 | Burbank |
| 2005/0230292 A1 | 10/2005 | Beden |
| 2005/0240233 A1 | 10/2005 | Lippert |
| 2006/0064053 A1 | 3/2006 | Bollish |
| 2006/0091056 A1 | 5/2006 | Brugger |
| 2006/0113249 A1 | 6/2006 | Childers |
| 2006/0117859 A1 | 6/2006 | Liu |
| 2006/0122552 A1 | 6/2006 | OMahony |
| 2006/0195064 A1 | 8/2006 | Plahey |
| 2006/0226057 A1 | 10/2006 | Robinson |
| 2006/0226090 A1 | 10/2006 | Robinson |
| 2006/0241543 A1 | 10/2006 | Gura |
| 2006/0289342 A1 | 12/2006 | Sugioka |
| 2007/0060786 A1 | 3/2007 | Gura |
| 2007/0088333 A1 | 4/2007 | Levin |
| 2007/0112297 A1 | 5/2007 | Plahey |
| 2007/0158249 A1 | 7/2007 | Ash |
| 2007/0158268 A1 | 7/2007 | DeComo |
| 2007/0161113 A1 | 7/2007 | Ash |
| 2007/0179425 A1 | 8/2007 | Gura |
| 2007/0213654 A1 | 9/2007 | Lundtveit |
| 2007/0253463 A1 | 11/2007 | Perry |
| 2007/0276328 A1 | 11/2007 | Childers |
| 2008/0006570 A1 | 1/2008 | Gura |
| 2008/0021366 A1 | 1/2008 | Gura |
| 2008/0041136 A1 | 2/2008 | Kopelman |
| 2008/0041792 A1 | 2/2008 | Crnkovich |
| 2008/0051689 A1 | 2/2008 | Gura |
| 2008/0058696 A1 | 3/2008 | Gura |
| 2008/0065006 A1 | 3/2008 | Roger |
| 2008/0077068 A1 | 3/2008 | Orr |
| 2008/0149563 A1 | 6/2008 | Ash |
| 2008/0154170 A1 | 6/2008 | Lannoy |
| 2008/0195021 A1 | 8/2008 | Roger |
| 2008/0195060 A1 | 8/2008 | Roger |
| 2008/0208103 A1 | 8/2008 | Demers |
| 2008/0217245 A1 | 9/2008 | Rambod |
| 2008/0230450 A1 | 9/2008 | Burbank |
| 2008/0258735 A1 | 10/2008 | Quackenbush |
| 2008/0264498 A1 | 10/2008 | Thompson |
| 2008/0290974 A1 | 11/2008 | Adams |
| 2009/0004053 A1 | 1/2009 | Kenley |
| 2009/0008306 A1 | 1/2009 | Cicchello |
| 2009/0008331 A1 | 1/2009 | Wilt |
| 2009/0010627 A1 | 1/2009 | Lindsay |
| 2009/0012450 A1 | 1/2009 | Shah |
| 2009/0045153 A1* | 2/2009 | Veeser | A47J 39/02 211/126.15 |
| 2009/0076434 A1 | 3/2009 | Mischelevich |
| 2009/0079578 A1 | 3/2009 | Dvorsky |
| 2009/0080757 A1 | 3/2009 | Roger |
| 2009/0082646 A1 | 3/2009 | Bouton |
| 2009/0082647 A1 | 3/2009 | Busby |
| 2009/0082649 A1 | 3/2009 | Muller |
| 2009/0082653 A1 | 3/2009 | Rohde |
| 2009/0082676 A1 | 3/2009 | Bennison |
| 2009/0083331 A1 | 3/2009 | Oh |
| 2009/0095679 A1 | 4/2009 | Demers |
| 2009/0101549 A1 | 4/2009 | Kamen |
| 2009/0101552 A1 | 4/2009 | Fulkerson |
| 2009/0101577 A1 | 4/2009 | Fulkerson |
| 2009/0105627 A1 | 4/2009 | Rohde |
| 2009/0107902 A1 | 4/2009 | Childers |
| 2009/0112155 A1 | 4/2009 | Zhao |
| 2009/0112507 A1 | 4/2009 | Edney |
| 2009/0113335 A1 | 4/2009 | Sandoe |
| 2009/0114037 A1 | 5/2009 | Smith |
| 2009/0120864 A1 | 5/2009 | Fulkerson |
| 2009/0124963 A1 | 5/2009 | Hogard |
| 2009/0127193 A1 | 5/2009 | Updyke |
| 2009/0127793 A1 | 5/2009 | Ferris |
| 2009/0137940 A1 | 5/2009 | Orr |
| 2009/0173682 A1 | 7/2009 | Robinson |
| 2009/0282980 A1 | 11/2009 | Gura |

(56) References Cited

U.S. PATENT DOCUMENTS

| | | |
|---|---|---|
| 2009/0294339 A1 | 12/2009 | Biewer |
| 2009/0312694 A1 | 12/2009 | Bedingfield |
| 2010/0022936 A1 | 1/2010 | Gura |
| 2010/0078381 A1 | 4/2010 | Merchant |
| 2010/0078387 A1 | 4/2010 | Wong |
| 2010/0084330 A1 | 4/2010 | Wong |
| 2010/0094193 A1 | 4/2010 | Gura |
| 2010/0100034 A1 | 4/2010 | Wich-Heiter |
| 2010/0101664 A1 | 4/2010 | Yamamoto |
| 2010/0116048 A1 | 5/2010 | Fulkerson |
| 2010/0116740 A1 | 5/2010 | Fulkerson |
| 2010/0129247 A1 | 5/2010 | Lauer |
| 2010/0133153 A1 | 6/2010 | Beden |
| 2010/0140149 A1 | 6/2010 | Fulkerson |
| 2010/0179464 A1 | 7/2010 | Smith |
| 2010/0184198 A1 | 7/2010 | Joseph |
| 2010/0192686 A1 | 8/2010 | Kamen |
| 2010/0209300 A1 | 8/2010 | Dirac |
| 2010/0234786 A1 | 9/2010 | Fulkerson |
| 2010/0252490 A1 | 10/2010 | Fulkerson |
| 2010/0312161 A1 | 12/2010 | Jonsson |
| 2010/0326911 A1 | 12/2010 | Rosenbaum |
| 2010/0326916 A1 | 12/2010 | Wrazel |
| 2010/0331754 A1 | 12/2010 | Fulkerson |
| 2011/0000830 A1 | 1/2011 | Ikeda |
| 2011/0000832 A1 | 1/2011 | Kelly |
| 2011/0009799 A1 | 1/2011 | Mullick |
| 2011/0017665 A1 | 1/2011 | Updyke |
| 2011/0028881 A1 | 2/2011 | Basaglia |
| 2011/0028882 A1 | 2/2011 | Basaglia |
| 2011/0041928 A1 | 2/2011 | Volker |
| 2011/0046533 A1 | 2/2011 | Stefani |
| 2011/0054352 A1 | 3/2011 | Ko |
| 2011/0054378 A1 | 3/2011 | Fulkerson |
| 2011/0071465 A1 | 3/2011 | Wang |
| 2011/0083746 A1 | 4/2011 | Hoang |
| 2011/0087187 A1 | 4/2011 | Beck |
| 2011/0092907 A1 | 4/2011 | Krogh |
| 2011/0093294 A1 | 4/2011 | Elahi |
| 2011/0098545 A1 | 4/2011 | Ross |
| 2011/0098624 A1 | 4/2011 | McCotter |
| 2011/0098625 A1 | 4/2011 | Masala |
| 2011/0098635 A1 | 4/2011 | Helmore |
| 2011/0105877 A1 | 5/2011 | Wilt |
| 2011/0105981 A1 | 5/2011 | Wagner |
| 2011/0105983 A1 | 5/2011 | Kelly |
| 2011/0105984 A1 | 5/2011 | Patel |
| 2011/0106002 A1 | 5/2011 | Helmore |
| 2011/0106047 A1 | 5/2011 | Burbank |
| 2011/0106466 A1 | 5/2011 | Furmanksi |
| 2011/0107251 A1 | 5/2011 | Guaitoli |
| 2011/0108482 A1 | 5/2011 | Lovell |
| 2011/0125073 A1 | 5/2011 | Rambod |
| 2011/0126714 A1 | 6/2011 | Brugger |
| 2011/0132838 A1 | 6/2011 | Curtis |
| 2011/0132841 A1 | 6/2011 | Rohde |
| 2011/0137224 A1 | 6/2011 | Ibragimov |
| 2011/0137264 A1 | 6/2011 | Chelak |
| 2011/0139704 A1 | 6/2011 | Choi |
| 2011/0140896 A1 | 6/2011 | Menzel |
| 2011/0141116 A1 | 6/2011 | Dalesch |
| 2011/0152739 A1 | 6/2011 | Roncadi |
| 2011/0155657 A1 | 6/2011 | Collins |
| 2011/0160649 A1 | 6/2011 | Pan |
| 2011/0166507 A1 | 7/2011 | Childers |
| 2011/0168614 A1 | 7/2011 | Pouchoulin |
| 2011/0171713 A1 | 7/2011 | Bluchel |
| 2011/0189048 A1 | 8/2011 | Curtis |
| 2011/0208072 A1 | 8/2011 | Pfeiffer |
| 2011/0208106 A1 | 8/2011 | Levin |
| 2011/0213289 A1 | 9/2011 | Toyoda |
| 2011/0218475 A1 | 9/2011 | Brugger |
| 2011/0218487 A1 | 9/2011 | Shang |
| 2011/0226680 A1 | 9/2011 | Jonsson |
| 2011/0230814 A1 | 9/2011 | Kopperschmidt |
| 2011/0232388 A1 | 9/2011 | Butterfield |
| 2011/0233162 A1* | 9/2011 | Kundinger, Jr. ..... A47B 47/027 211/79 |
| 2011/0237997 A1 | 9/2011 | Beden |
| 2011/0237998 A1 | 9/2011 | Wariar |
| 2011/0240537 A1 | 10/2011 | Ferrarini |
| 2011/0240555 A1 | 10/2011 | Ficheux |
| 2011/0269167 A1 | 11/2011 | Bene |
| 2011/0272337 A1 | 11/2011 | Palmer |
| 2011/0272352 A1 | 11/2011 | Braig |
| 2011/0275984 A1 | 11/2011 | Biewer |
| 2011/0284464 A1 | 11/2011 | Roncadi |
| 2011/0297593 A1 | 12/2011 | Kelly |
| 2011/0297598 A1 | 12/2011 | Lo |
| 2011/0297599 A1 | 12/2011 | Lo |
| 2011/0300010 A1 | 12/2011 | Jamagin |
| 2011/0300230 A1 | 12/2011 | Peterson |
| 2011/0303588 A1 | 12/2011 | Kelly |
| 2011/0303590 A1 | 12/2011 | Childers |
| 2011/0303598 A1 | 12/2011 | Lo |
| 2011/0309019 A1 | 12/2011 | Ahrens |
| 2011/0315611 A1 | 12/2011 | Fulkerson |
| 2011/0319823 A1 | 12/2011 | Bojan |
| 2012/0010554 A1 | 1/2012 | Vantard |
| 2012/0018377 A1 | 1/2012 | Tsukamoto |
| 2012/0018378 A1 | 1/2012 | Kelly |
| 2012/0022440 A1 | 1/2012 | Childers |
| 2012/0029324 A1 | 2/2012 | Akonur |
| 2012/0029937 A1 | 2/2012 | Neftel |
| 2012/0031826 A1 | 2/2012 | Childers |
| 2012/0035534 A1 | 2/2012 | Yu |
| 2012/0037550 A1 | 2/2012 | Childers |
| 2012/0043279 A1 | 2/2012 | Kelly |
| 2012/0065567 A1 | 3/2012 | Zarate |
| 2012/0075266 A1 | 3/2012 | Shimizu |
| 2012/0214117 A1 | 8/2012 | Broker |
| 2012/0259282 A1 | 10/2012 | Alderete |
| 2013/0126413 A1 | 5/2013 | Van Der Merwe |
| 2013/0140652 A1 | 6/2013 | Erdler |
| 2013/0184638 A1 | 7/2013 | Scarpaci |
| 2013/0199998 A1 | 8/2013 | Kelly |
| 2013/0220907 A1 | 8/2013 | Fulkerson |
| 2013/0233395 A1 | 9/2013 | Dinh |
| 2013/0292319 A1 | 11/2013 | Fulkerson |
| 2014/0199193 A1 | 7/2014 | Wilt |
| 2015/0083647 A1 | 3/2015 | Meyer |

FOREIGN PATENT DOCUMENTS

| | | |
|---|---|---|
| CN | 1146728 | 4/1997 |
| CN | 1235849 A | 11/1999 |
| CN | 1471617 A | 1/2004 |
| CN | 101175514 | 5/2008 |
| CN | 101254324 A | 9/2008 |
| CN | 101269247 | 9/2008 |
| CN | 101311589 | 11/2008 |
| CN | 101801432 | 8/2010 |
| CN | 201600175 U | 10/2010 |
| CN | 101977642 | 2/2011 |
| CN | 102596283 A | 7/2012 |
| CN | 102639201 A | 8/2012 |
| CN | 103476486 A | 12/2013 |
| EP | 0110514 A1 | 6/1984 |
| EP | 0121085 | 10/1984 |
| EP | 0121085 A1 | 10/1984 |
| EP | 0808633 | 11/1997 |
| EP | 2237814 | 10/2010 |
| GB | 1579177 | 11/1980 |
| JP | S50126866 A | 10/1975 |
| JP | S56138580 U | 10/1981 |
| JP | S5755010 U | 3/1982 |
| JP | S5913770 U | 1/1984 |
| JP | S59127978 U | 8/1984 |
| JP | S6037674 U | 3/1985 |
| JP | S60108870 | 6/1985 |
| JP | S60108870 U | 7/1985 |
| JP | S63202882 A | 8/1988 |
| JP | S63192912 U | 12/1988 |
| JP | H02114269 U | 9/1990 |

(56) References Cited

FOREIGN PATENT DOCUMENTS

| | | |
|---|---|---|
| JP | H0413143 U | 2/1992 |
| JP | 005176991 A | 7/1993 |
| JP | H05172268 A | 9/1993 |
| JP | H06230023 A | 8/1994 |
| JP | H07504507 A | 5/1995 |
| JP | H08511094 | 11/1996 |
| JP | H11137673 A | 5/1999 |
| JP | 2002119585 A | 4/2002 |
| JP | 2002139165 A | 5/2002 |
| JP | 2002523772 | 7/2002 |
| JP | 2002527148 | 8/2002 |
| JP | 2003502091 | 1/2003 |
| JP | 2004057284 | 2/2004 |
| JP | 3126509 U | 11/2006 |
| JP | 2008055185 A | 3/2008 |
| JP | 2008291911 A | 4/2008 |
| JP | 2008511094 A | 4/2008 |
| JP | 2008531192 | 8/2008 |
| JP | 2008531192 A | 8/2008 |
| JP | 2008531192 A1 | 8/2008 |
| JP | 2009521965 | 6/2009 |
| JP | 2012510826 | 5/2012 |
| JP | 2012510826 A | 5/2012 |
| MX | 20103880 | 7/2010 |
| TW | 200824731 A | 6/2008 |
| WO | 1980002806 | 12/1980 |
| WO | 9318380 A1 | 9/1993 |
| WO | 199318380 | 9/1993 |
| WO | 1993018380 A1 | 9/1993 |
| WO | 9420154 A1 | 9/1994 |
| WO | 9428386 A1 | 12/1994 |
| WO | 199428386 | 12/1994 |
| WO | 1996025214 | 8/1996 |
| WO | 1997027490 | 7/1997 |
| WO | 9823353 | 6/1998 |
| WO | 1999030757 A1 | 6/1999 |
| WO | 0021590 A1 | 4/2000 |
| WO | 20015069412 A1 | 7/2001 |
| WO | 2003099354 | 12/2003 |
| WO | 2003101510 A1 | 12/2003 |
| WO | 2004009158 A2 | 1/2004 |
| WO | 2005065126 A2 | 7/2005 |
| WO | 2005089832 A2 | 9/2005 |
| WO | 200609362 | 9/2006 |
| WO | 2006120415 | 11/2006 |
| WO | 2007028056 | 3/2007 |
| WO | 2007140241 A1 | 12/2007 |
| WO | 2008053259 A1 | 5/2008 |
| WO | 2008129830 A1 | 10/2008 |
| WO | 2009042181 A1 | 4/2009 |
| WO | 2009045589 A2 | 4/2009 |
| WO | 2009065598 | 5/2009 |
| WO | 2009073567 | 6/2009 |
| WO | 2009091963 | 7/2009 |
| WO | 2009157877 | 12/2009 |
| WO | 201042666 A2 | 4/2010 |
| WO | 2010042666 | 4/2010 |
| WO | 2010042666 A2 | 4/2010 |
| WO | 2010042667 | 4/2010 |
| WO | 2010062698 | 6/2010 |
| WO | 2010062698 A2 | 6/2010 |
| WO | 2010081121 | 7/2010 |
| WO | 2010081121 A1 | 7/2010 |
| WO | 2010114932 | 10/2010 |
| WO | 2012108910 | 8/2012 |
| WO | 2014105267 A1 | 7/2014 |
| WO | 2014105755 | 7/2014 |
| WO | 2014161008 | 10/2014 |

OTHER PUBLICATIONS

Anthony J. Wing et al., 'Dialysate Regeneration', Replacement of Renal Function by Dialysis, Chapter 17, 323-340 (William Drukker et al., eds., Martinus Nijhoff Publishers, 2nd ed., 1983).

CD Medical, Inc., 'Operator's Manual Drake Willock 480 Ultrafiltration Control Single Patient Delivery System', 1988.

Cobe Laboratories, Inc., 'CentrySystem 3 Dialysis Control Unit Operators Manual', Sep. 1988.

Fresenius AG, 'Acumen Acute Dialysis Machine Operating Instructions', Version 1.0, May 1996.

International Preliminary Report on Patentability for PCT/US2009/059907, dated Apr. 15, 2010, Fresenius Medical Care Holdings, Inc.

International Search Report for PCT/US09/59907, Xcorporeal, Inc., dated Apr. 13, 2010.

Manns et al., 'The acu-men: A New Device for Continuous Renal Replacement Therapy in Acute Renal Failure', Kidney International, vol. 54 (1998), 268-274.

NxStage Medical, Inc., 'NxStage System One User's Guide', Software Version 4.3, Part 1 through Part 6-20, 2006.

NxStage Medical, Inc., 'NxStage System One User's Guide', Software Version 4.3, Part 6-20 through Part C-17, 2006.

REDY 2000 Operator's Manual (1991) (Sorbent cartridge-based hemodialysis system).

REDY 2000 Service Manual (1989) (Sorbent cartridge-based hemodialysis system).

Renal Solutions, Inc., 'Dialysate Tubing Set and Dialysate Reservoir Bag for the Allient Sorbent Hemodialysis System', Instructions, 2004.

Renal Solutions, Inc., 510(K) for the SORB+ and HISORB+ Cartridges, Mar. 31, 2003.

Renal Solutions, Portions of the Allient Sorbent Hemodialysis System, Home User Manual, 2006, Chapters 1-3.

Reyes et al., 'Acid-Base Derangements During Sorbent Regenerative Hemodialysis in Mechanically Ventilated Patients', Critical Care Medicine, vol. 19, No. 4, 1991, 554-559 (col. 2, lines 17-22).

Seratron Dialysis Control System Operations Manual (cumulative 1980).

Ward et al., 'Sorbent Dialysis Regenerated Dialysis Delivery Systems', Peritoneal Dialysis Bulletin, Chapters, 3(2): S41-S48 (Apr.-Jun. 1983).

COBE Renal Care, Inc., "Sorbent Dialysis Primer", Edition 4, Sep. 1993.

Fresenius USA, Inc., "Fresenius 2008H Hemodialysis Machine", Part No. 490005, Revision H, 1994-2001.

International Search Report for PCT/US09/31228, Xcorporeal, Inc., dated Jun. 19, 2009.

International Search Report for PCT/US09/59906, Xcorporeal, Inc., dated May 8, 2012.

International Search Report for PCT/US09/62840, Xcorporeal, Inc. dated Feb. 10, 2012.

International Search Report for PCT/US10/20698, Xcorporeal, Inc., dated Jun. 16, 2010.

International Search Report for PCT/US10/29500, Xcorporeal, Inc., dated Jul. 2, 2010.

International Search Report for PCT/US11/53184, Xcorporeal, Inc., dated Mar. 2, 2012.

International Search Report for PCT/US13/77234, dated Jun. 9, 2014.

International Search Report PCT/US08/85062, dated Mar. 20, 2009, XCorporeal, Inc.

Renal Solutions, Inc., Portions of 510(k) Allient Sorbent Hemodialysis System (Allient Main Controller Software Architecture Overview), Renal Solutions, Inc., dated Dec. 17, 2004.

Renal Solutions, Inc., Portions of 510(k) Allient Sorbent Hemodialysis System (Sections A-I), Dec. 17, 2004.

Renal Solutions, Inc., Portions of 510(k) Allient Sorbent Hemodialysis System (Sections M.3 and M.4), Renal Solutions, Inc., Dec. 17, 2004.

Renal Solutions, Portions of the Allient Sorbent Hemodialysis System, Home User Manual, 2006, Chapters 4.

Renal Solutions, Portions of the Allient Sorbent Hemodialysis System, Home User Manual, 2006, Chapters 5 to end.

Renal Solutions, Portions of the Allient Sorbent Hemodialysis System, Operator Manual, 2008, Chapter 3.

Renal Solutions, Portions of the Allient Sorbent Hemodialysis System, Operator Manual, 2008, Chapter 4, 4-1 to 4-33.

(56) References Cited

OTHER PUBLICATIONS

Renal Solutions, Portions of the Allient Sorbent Hemodialysis System, Operator Manual, 2008, Chapter 4, 4-34 to 4-69.
Renal Solutions, Portions of the Allient Sorbent Hemodialysis System, Operator Manual, 2008, Chapter 5.
Renal Solutions, Portions of the Allient Sorbent Hemodialysis System, Operator Manual, 2008, Chapters 1 to 2.
Renal Solutions, Portions of the Allient Sorbent Hemodialysis System, Operator Manual Model 1500, 2008, Chapter 3, 3-2 to 3-30.
Renal Solutions, Portions of the Allient Sorbent Hemodialysis System, Operator Manual Model 1500, 2008, Chapter 3, 3-31 to 3-70.
Renal Solutions, Portions of the Allient Sorbent Hemodialysis System, Operator Manual Model 1500, 2008, Chapters 1 to 2.
Renal Solutions, Special 510(k) Device Modification, Allient Sorbent Hemodialysis System, Mar. 15, 2007.
International Search Report for PCT/US2013/068506, dated Apr. 9, 2014.
International Preliminary Report on Patentability for PCT/US13/77234, dated Jun. 30, 2015.
International Search Report for PCT/US14/60122, dated Jan. 21, 2015.
International Search Report for PCT/US14/35051, Sep. 5, 2014.

\* cited by examiner

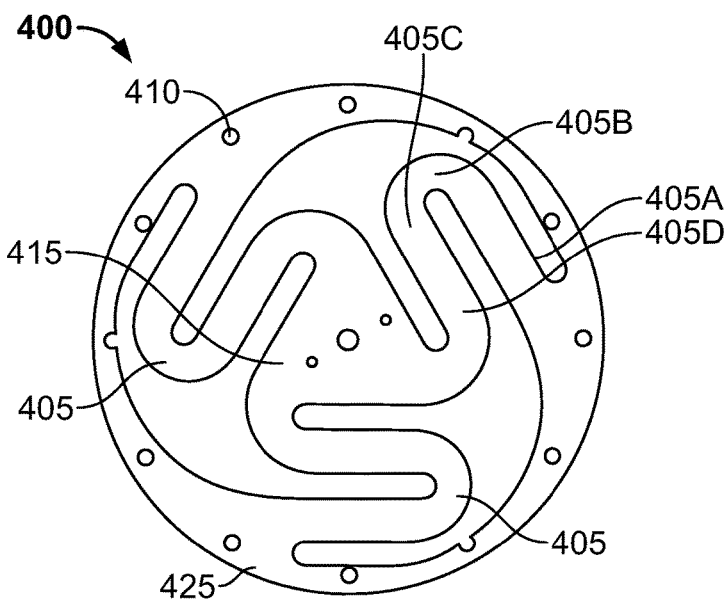
FIG. 4A
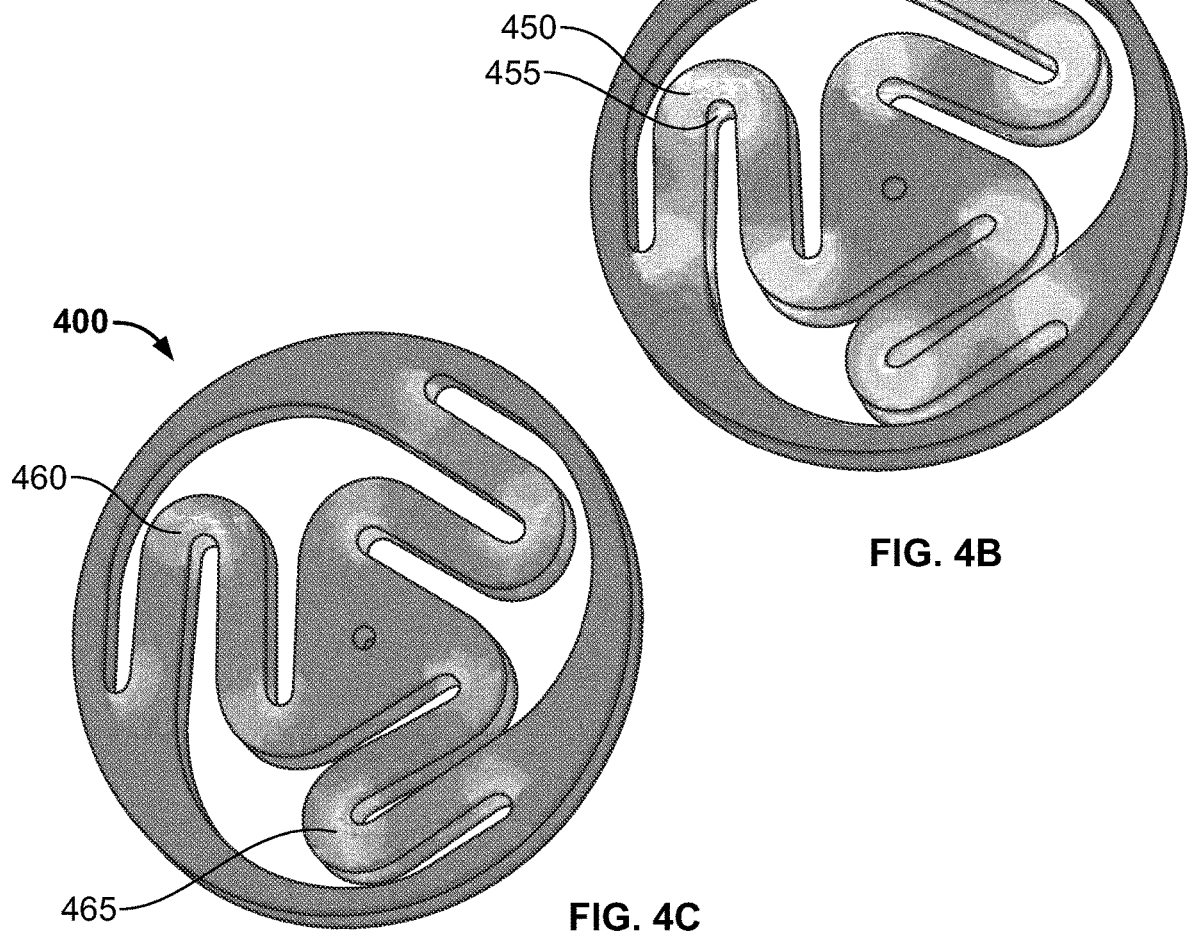
FIG. 4B
FIG. 4C

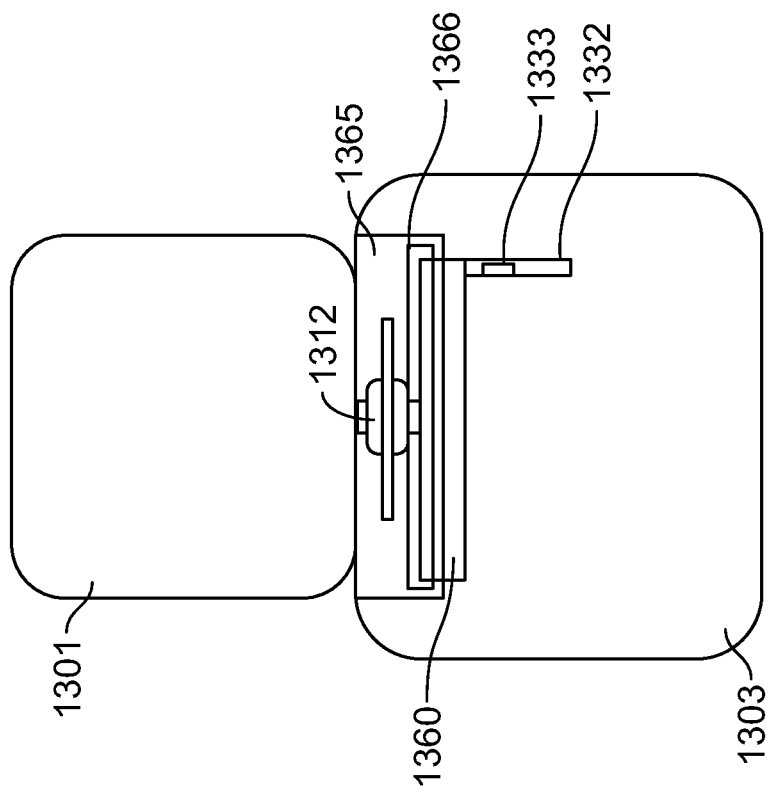
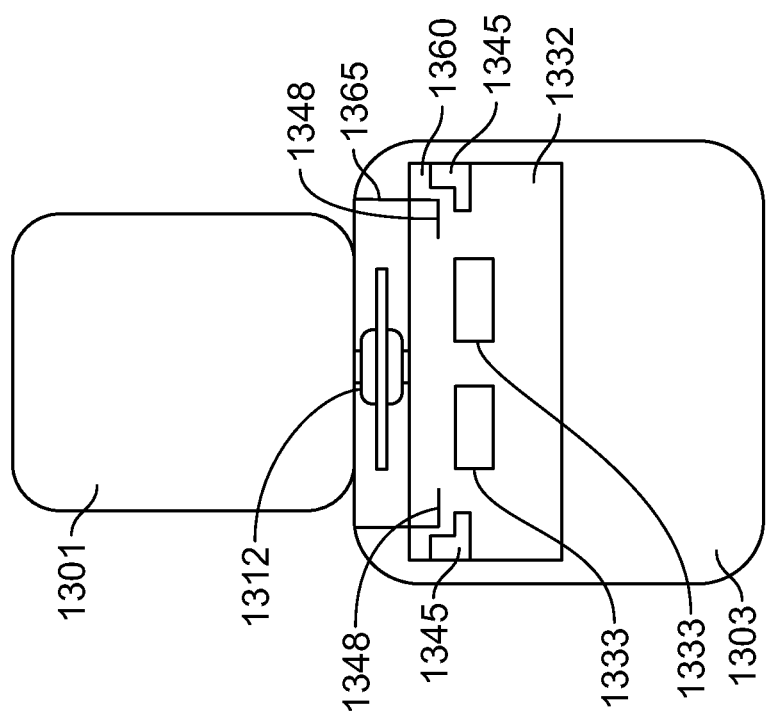
FIG. 13B
FIG. 13A

DIALYSIS SYSTEMS WITH A SUSPENDED RESERVOIR

CROSS-REFERENCE

The present application is a continuation application of U.S. patent application Ser. No. 15/808,189, entitled "Load Suspension and Weighing System for a Dialysis Machine Reservoir" and filed on Nov. 9, 2017, which is a continuation application of U.S. patent application Ser. No. 14/848,012, of the same title, filed on Sep. 8, 2015, and issued as U.S. Pat. No. 9,841,310 on Dec. 12, 2017, which is a continuation application of U.S. patent application Ser. No. 13/726,450, of the same title, filed on Dec. 24, 2012, and issued as U.S. Pat. No. 9,157,786 on Oct. 13, 2015.

FIELD

The present specification relates generally to portable dialysis systems. More particularly, the present specification relates to a load suspension and weighing system for a removable reservoir unit of a portable dialysis machine.

BACKGROUND

Blood purification systems, which are used for conducting hemodialysis, hemodiafiltration or hemofiltration, involve the extracorporeal circulation of blood through an exchanger having a semi permeable membrane. Such systems further include a hydraulic system for circulating blood and a hydraulic system for circulating replacement fluid or dialysate comprising blood electrolytes in concentrations close to those of the blood of a healthy subject. Most of the conventionally available blood purification systems are, however, quite bulky in size and difficult to operate. Further, the design of these systems makes them unwieldy and not conducive to the use and installation of disposable components.

Standard dialysis treatment, using an installed apparatus in hospitals, comprises two phases, namely, (a) dialysis, in which toxic substances and scoriae (normally small molecules) pass through the semi-permeable membrane from the blood to the dialysis liquid, and (b) ultrafiltration, in which a pressure difference between the blood circuit and the dialysate circuit, more precisely a reduced pressure in the latter circuit, causes the blood content of water to be reduced by a predetermined amount.

Dialysis procedures using standard equipment tend to be cumbersome as well as costly, besides requiring the patient to be bound to a dialysis center for long durations. While portable dialysis systems have been developed, conventional portable dialysis systems suffer from certain disadvantages. First, they are not sufficiently modular, thereby preventing the easy setup, movement, shipping, and maintenance of the systems. Second, the systems are not simplified enough for reliable, accurate use by a patient. The systems' interfaces and methods of using disposable components are subject to misuse and/or errors in usage by patients. For a portable dialysis system to be truly effective, it should be easily and readily used by individuals who are not health-care professionals, with disposable input and data input sufficiently constrained to prevent inaccurate use.

There is also a need for a portable system that can effectively provide the functionality of a dialysis system in a safe, cost-effective, and reliable manner. In particular, there is a need for a compact dialysis fluid reservoir system that can satisfy the fluid delivery requirements of a dialysis procedure while integrating therein various other critical functions, such as fluid heating, fluid measurement and monitoring, leak detection, and disconnection detection. The reservoir system must be weighed consistently and accurately to insure that the amount of water in the reservoir is always known and so volumetric controls can be applied based on the calculated water levels. In addition, since the reservoir system is subject to insertion into and removal from the dialysis machine by the user, it must be configured to minimize the possibility that variance in weight measurement will be generated by an improper positioning of the reservoir pan or leakage of water onto the weight measurement system. Therefore, a need exists for a weight measurement system that can effectively measure the liquid level in a reservoir system.

To address these needs, U.S. patent application Ser. No. 13/023,490, which is entitled "Portable Dialysis Machine", filed on Feb. 8, 2011, assigned to the applicant of the present application, and herein incorporated by reference in its entirety, describes a "dialysis machine comprising: a controller unit wherein said controller unit comprises: a door having an interior face; a housing with a panel wherein said housing and panel define a recessed region configured to receive said interior face of said door; and a manifold receiver fixedly attached to said panel; a base unit wherein said base unit comprises: a planar surface for receiving a container of fluid; a scale integrated with said planar surface; a heater in thermal communication with said planar surface; and, a sodium sensor in electromagnetic communication with said planar surface."

The dialysis machine includes a reservoir unit for storing non-sterile water. Upon initiation of the dialysis machine, the water passes through a sorbent filtration process, then through a dialysis process, and finally back into the reservoir. The dialysis machine also includes a flexure system for flexibly receiving and suspending the reservoir pan and for measuring the water weight. The flexure system comprises a series of four flexures, each positioned at a corner of a rectangular shaped reservoir pan and each integrated with a Hall sensor. It has been found that the four cornered flexure system has certain functionalities that can be improved upon. Particularly, use of the four cornered flexure system may lead to weighing inaccuracies arising from oscillation of the system and creep arising from the averaging operation of data over the four flexure units. Therefore, what is needed is an improved reservoir unit weight measurement system configured to reduce weighing inaccuracies.

SUMMARY

The present specification is directed toward a flexure assembly for weighing and suspending loads. In one embodiment, the flexure assembly comprises a top assembly with a first plurality of magnets, a bottom assembly with a second plurality of magnets, where the first plurality of magnets and second plurality of magnets generate a magnetic field within the flexure assembly. The assembly further includes a circuit board positioned between the top assembly and bottom assembly. The circuit board has a plurality of magnetic field sensors and a processor. The assembly has at least one ring, a flexure ring, attached to the top assembly and positioned between the top assembly and the circuit board. The flexure ring has at least one curved arm for allowing movement, particularly vertical movement, of the top assembly in relation to the circuit board and in tandem with the bottom assembly. There is also at least one ring, a second flexure ring, attached to the bottom assembly and positioned between the bottom assembly and the circuit board. The second flexure ring has at least one curved arm for allowing movement, particularly vertical movement, of the bottom assembly in relation to the circuit board and in tandem with the top assembly.

In one embodiment, the flexure assembly comprises two flexure rings positioned between the top assembly and the circuit board and two flexure rings positioned between the bottom assembly and the circuit board.

In one embodiment, the top assembly is adapted to attach to an attachment point of a dialysis machine. The attachment point is positioned along a vertical axis extending through a center of said dialysis machine. In one embodiment, the bottom assembly is adapted to attach to an attachment point of a first internal frame of a dialysis machine. The attachment point of the first internal frame is positioned along a vertical axis extending through a center of said dialysis machine.

In one embodiment, the flexure assembly includes at least one spacer element between each of said at least one flexure rings and said circuit board.

In one embodiment, the flexure assembly further comprises copper wherein said copper is adapted to magnetically dampen mechanical oscillations of structures suspended from the flexure assembly and attached to the bottom assembly.

In one embodiment, the flexure rings are comprised of aluminum.

The present specification is also directed toward a method for weighing and suspending loads of a reservoir unit of a dialysis machine, comprising the steps of: providing a flexure assembly, said flexure assembly attached to a point along a vertical axis of said dialysis machine, where the flexure assembly includes a top assembly with a first plurality of magnets and a bottom assembly with a second plurality of magnets. The first plurality of magnets and second plurality of magnets generate a magnetic field within the flexure assembly. A circuit board is positioned between the top assembly and bottom assembly and includes a plurality of magnetic field sensors and a processor. At least one flexure ring is attached to the top assembly and positioned between the top assembly and the circuit board. The at least one flexure ring has at least one curved arm for allowing movement, particularly vertical movement, of the top assembly in relation to the circuit board and in tandem with the bottom assembly. There is at least one second flexure ring attached to the bottom assembly and positioned between the bottom assembly and the circuit board. The at least one second flexure ring has at least one curved arm for allowing movement, particularly vertical movement, of the bottom assembly in relation to the circuit board and in tandem with the top assembly. The weighing and suspension process further comprises the steps of applying a load to the bottom assembly of said flexure assembly, wherein the application of the load pulls on the flexure assembly, resulting in the displacement of the magnetic field about the circuit board, sensing the magnetic field displacement using the plurality of sensors, generating a voltage output from the sensors to the processor and using said processor to determine a weight measurement based on the voltage output.

The present specification is also directed toward a system for weighing and suspending loads in a dialysis machine, said system comprising: a flexure assembly attached to the interior of said dialysis machine, said flexure assembly comprising: a top assembly comprising a first plurality of magnets; a bottom assembly comprising a second plurality of magnets, wherein said first plurality of magnets and said second plurality of magnets generate a magnetic field within said flexure assembly; a circuit board positioned between said top assembly and said bottom assembly and comprising a plurality of magnetic field sensors and a processor; at least one flexure ring attached to said top assembly and positioned between said top assembly and said circuit board, said at least one flexure ring comprising at least one curved arm for allowing movement of said top assembly in relation to said circuit board and in tandem with said bottom assembly; and at least one flexure ring attached to said bottom assembly and positioned between said bottom assembly and said circuit board, said at least one flexure ring comprising at least one curved arm for allowing movement of said bottom assembly in relation to said circuit board and in tandem with said top assembly; a first internal frame attached to said bottom assembly, said first internal frame comprising: a top plate attached to said bottom assembly; at least two tracks configured to slidably receive a reservoir unit; and, a back plate having a plurality of electrical contact elements configured to be in physical and electrical contact with a contact plate on said reservoir unit; and, a second internal frame attached, separately and independently from said first internal frame and flexure assembly, to the interior of said dialysis machine, said second internal frame comprising: a top section attached to said dialysis machine; at least two tracks configured to slidably receive a ceiling frame, said ceiling frame comprising: a lining bag configured to rest within said reservoir unit and contain a liquid; at least one tube for removing said liquid from said reservoir unit; and, at least one tube for returning said liquid to said reservoir unit.

In one embodiment, the system comprises two flexure rings positioned between said top assembly and said circuit board and two flexure rings positioned between said bottom assembly and said circuit board.

In one embodiment, the top assembly of the flexure assembly is adapted to attach to an attachment point of a dialysis machine, wherein said attachment point is positioned along a vertical axis extending through a center of said dialysis machine. In one embodiment, the bottom assembly of the flexure assembly is adapted to attach to an attachment point of a first internal frame of a dialysis machine, wherein said attachment point of the first internal frame is positioned along a vertical axis extending through a center of said dialysis machine.

In one embodiment, the flexure assembly includes at least one spacer element between each of said at least one flexure rings and said circuit board.

In one embodiment, the flexure assembly further comprises copper wherein said copper is adapted to magnetically dampen mechanical oscillations of structures suspended from the flexure assembly and attached to the bottom assembly.

In one embodiment, the flexure rings of the flexure assembly are comprised of aluminum.

The present specification is also directed toward a dialysis system having an assembly for weighing and suspending loads. The assembly comprises 1) a first component comprising a first plurality of magnets, such as 1, 2, 3, 4, 5, 6, 7, 8, 9, 10, or more magnets, 2) a second component comprising a second plurality of magnets, such as 1, 2, 3, 4, 5, 6, 7, 8, 9, 10, or more magnets, where the first plurality of magnets and the second plurality of magnets generate a magnetic field within the assembly and 3) a circuit board positioned between the first component and the second component and comprising a plurality of magnetic field sensors, such as 1, 2, 3, 4, 5, 6, 7, 8, 9, 10, or more sensors, for outputting a voltage based on changes to said magnetic field and a processor, where the processor is configured to receive the voltage output from the sensors and output a weight measurement based on the voltage output.

Optionally, the dialysis system further comprises at least one flexing structure attached to the first component and positioned between the first component and the circuit board, the at least one flexing structure comprising at least one curved member for allowing movement of the first component in relation to the circuit board. The dialysis system further comprises at least one flexing structure attached to the second component and positioned between the second component and the circuit board, the at least one flexing structure comprising at least one curved member for allowing movement of the second component in relation to the circuit board.

Optionally, the dialysis system further comprises a first internal frame attached to the second component, the first internal frame having a top plate attached to the second component, at least two tracks configured to slidably receive a reservoir unit, and a plate having a plurality of electrical contact elements configured to be in physical and electrical contact with a contact plate on the reservoir unit.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the detailed description when considered in connection with the accompanying drawings:

FIG. 4A is an illustration of one embodiment of a flexure ring of the flexure assembly;

FIG. 4B is an illustration depicting the minimum and maximum points of stress on a flexure ring with an 18 KG load in accordance with one embodiment of the present specification;

FIG. 4C is an illustration depicting the minimum and maximum points of strain on a flexure ring with an 18 KG load in accordance with one embodiment of the present specification;

FIG. 13A is a front view illustration of one embodiment of a dialysis machine, depicting the flexure assembly and first and second frames therein;

FIG. 13B is a side view illustration of one embodiment of the dialysis machine of FIG. 13A, depicting the flexure assembly and first and second frames therein;

DETAILED DESCRIPTION

Figure 1A:
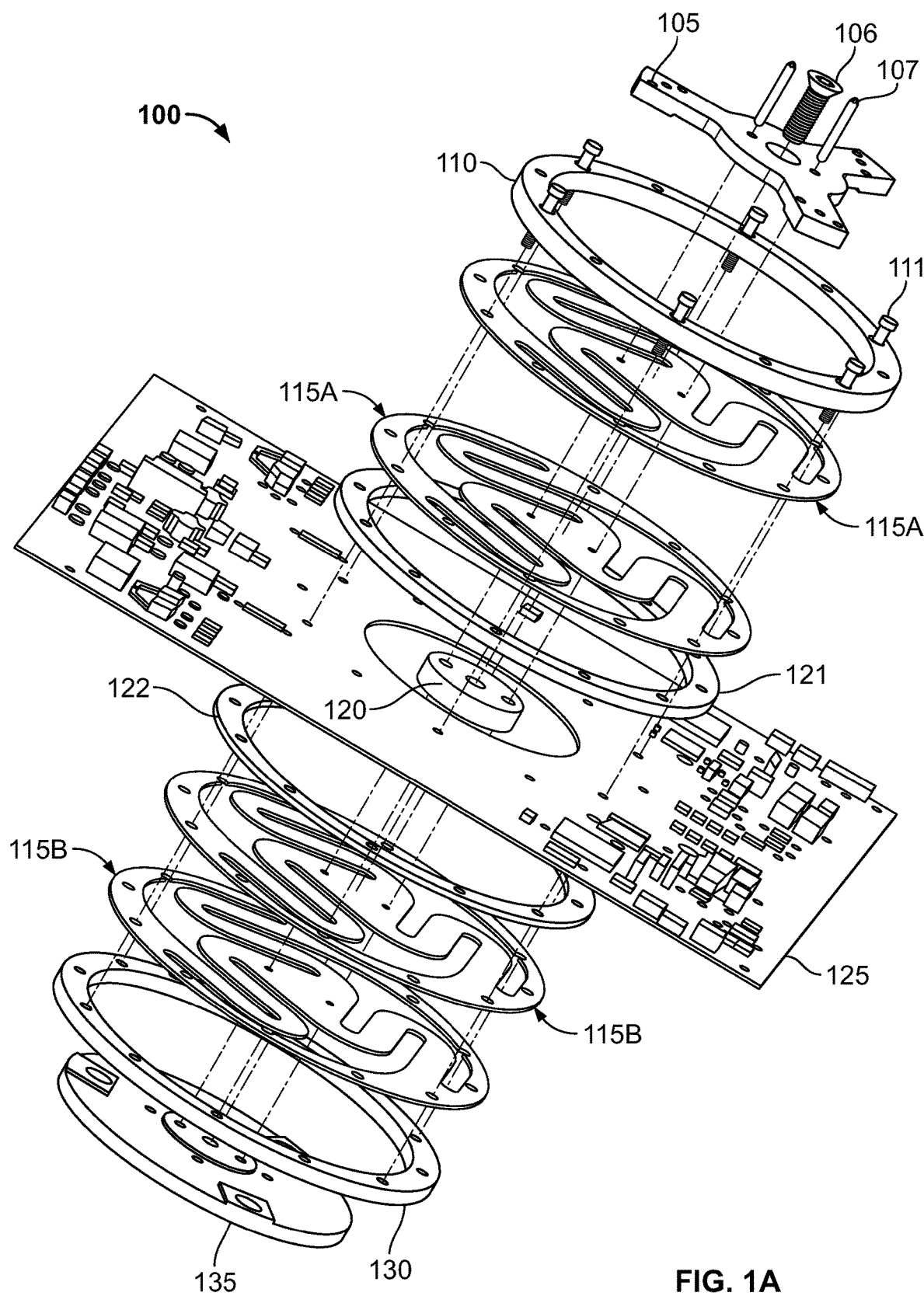
FIG. 1A is an illustration of one embodiment of a disassembled flexure assembly, depicting individual components of the assembly.

The present specification is directed toward a load suspension and weighing system for a reservoir unit of a portable dialysis machine. In one embodiment, the system comprises a single, centrally located flexure assembly rather than four separate flexures positioned each at a corner of a rectangular shaped reservoir unit, thereby eliminating weighing inaccuracies arising from averaging separate flexure data. In one embodiment, the flexure assembly is mounted to the underside surface of the top of a frame that defines a base unit within a dialysis machine. In one embodiment, the flexure assembly includes mounting plates, magnets, flexure rings, spacers, and a circuit board. Inexpensive hall sensors on the circuit board resistively sense changes in magnetic fields generated by movement of the magnets for calculation of weight measurements. The circuit board and hall sensors are stationary and two sets of magnets, one above the board and another below the board, move vertically in relation to the board and fixed in relation to each other. The hall sensors sense the change in the magnetic field as the sets of magnets move when a weight is applied. The change in the magnetic field causes an output in voltage from the hall sensors. A processor on the circuit board processes the voltage output to determine the weight. Use of a flexure assembly with one axis of movement provides a scale system that is low cost, reliable, robust and easy to assemble and integrate into the dialysis machine.

A first internal frame, used for supporting the reservoir unit, is mounted to the underside of the flexure assembly. In one embodiment, the first internal frame includes a top plate, a back plate housing electrical contact elements, and two tracks for suspending the reservoir unit. The reservoir unit is slid onto the tracks of the first internal frame and comes to rest within the dialysis machine such that an electrical contact plate on the insertion side of the reservoir unit is in physical contact and alignment with the electrical contact elements of the first internal frame. By being integrated with the first internal frame and positioned above the reservoir unit, the flexure assembly provides accurate and consistent weight measurements of the reservoir contents and avoids being damaged by fluids spilling out of the reservoir.

The present specification discloses multiple embodiments. The following disclosure is provided in order to enable a person having ordinary skill in the art to practice the claimed embodiments. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1B:
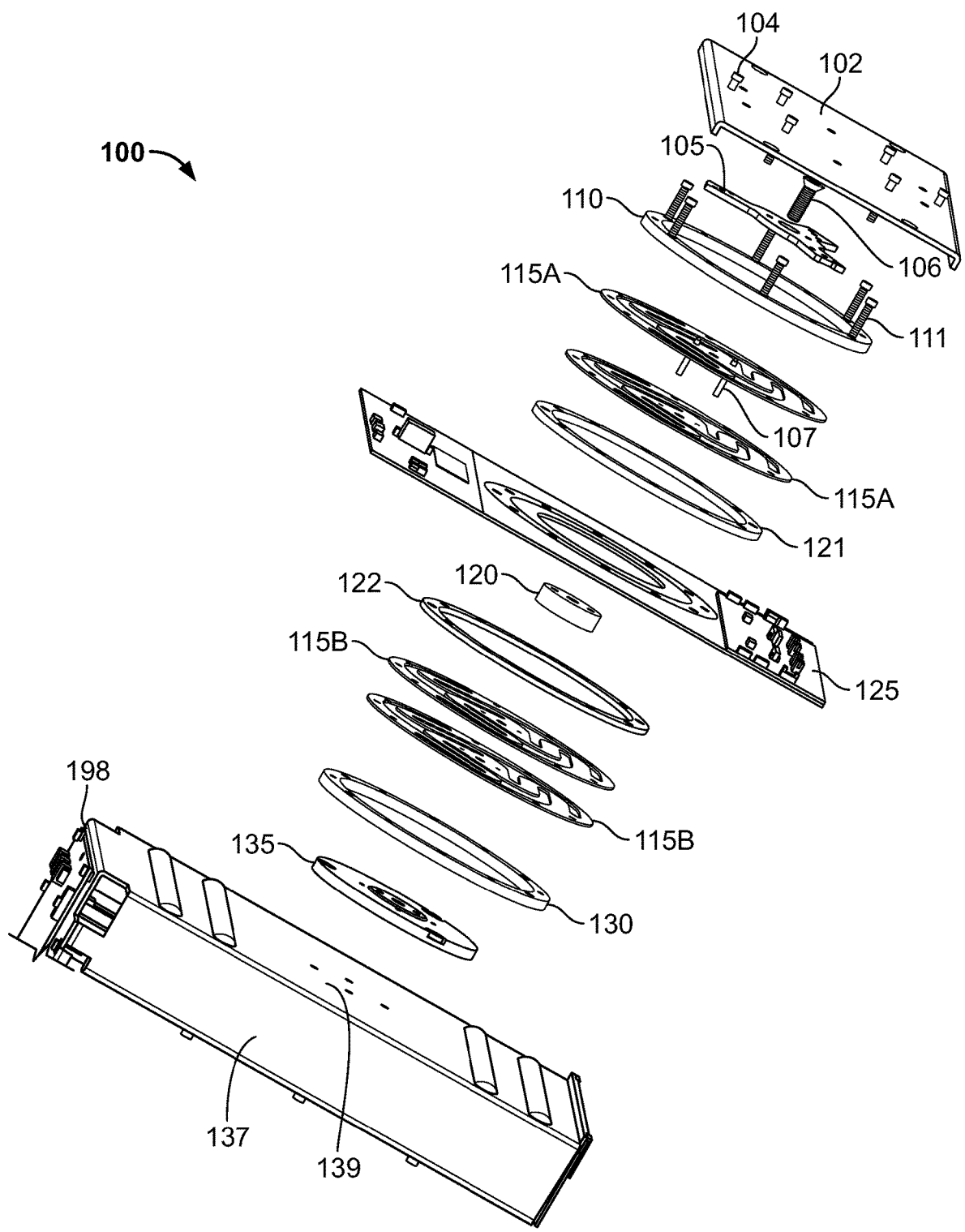
FIG. 1B is an illustration of the embodiment of a disassembled flexure assembly of FIG. 1A, further depicting a scale support and pan holder for mounting of the assembly within a dialysis machine.

FIGS. 1A and 1B are illustrations of one embodiment of a disassembled flexure assembly 100, depicting individual components of the assembly 100. As can be seen in FIG. 1B, the assembly 100 connects to a scale support plate 102 adapted to be connected to a frame of the dialysis machine via a top ring clamp 110. In one embodiment, the top ring clamp 110 is secured to the scale support 102 via six screws 104 which pass through the support 102 and into holes in the clamp 110. Two dowel pins 107 insert into the top center ring 105 of the flexure assembly 100 and provide a means for aligning and securing the components of the flexure assembly 100 together.

Referring to both FIGS. 1A and 1B, the top center ring 105 has a hole at its center for the passage of a center screw 106. The center screw 106 passes through to the center ring 135 at the bottom of the flexure assembly 100, securing the entire flexure assembly 100 together. The top ring clamp 110 is secured to the bottom tapped ring clamp 130 by screws 111. Preferably, the top ring clamp 110 is mounted to the dialysis housing frame, which is the central frame around which the housing of at least a bottom unit of a dialysis machine is formed, thereby insuring that any load placed on the system is translated through the load and suspension assembly directly to the strongest structure within the dialysis machine and avoiding placing any load on delicate structures, such as the reservoir assembly controller board 125.

In one embodiment, the top center ring 105 is a spoke structure comprising an internal central hub with three spokes extending therefrom. The top ring clamp 110 is ring shaped and includes a plurality of screws 111 which pass through holes along the periphery of the remaining components of the assembly 100 and secure to a corresponding bottom ring clamp 130. The flexure assembly 100 is secured to the first internal frame 198 at the bottom center ring 135. Referring to FIG. 1B, the first internal frame 198 includes a pan holder 137 with four screw holes 139 proximate its center. Screws pass through the holes 139 in the pan holder 137 and secure into corresponding screw holes in the bottom tapped center ring 135.

In one embodiment, in addition to a top plate member for attachment to the flexure assembly, the first internal frame 198 includes two tracks for suspending a reservoir unit and a back plate with electrical contact elements. In one embodiment, the reservoir unit includes an electrical contact plate on its insertion side which comes into contact with the first internal frame's contact elements when the reservoir unit is fully inserted into the dialysis machine. A second internal frame suspends a ceiling frame that includes a bag to hold the liquid in the reservoir and tubing to remove liquid from, and return liquid to, the reservoir. The second internal frame is attached to the dialysis machine separately and independently from the first internal frame and is not involved in weight measurement calculations.

The load weighing and suspension assembly 100, also referred to as a flexure assembly 100, further includes a plurality of flexing structures. A flexing structure is any component with a portion of it being substantially planar and has a member, arm, structure, or other component that flexes or bends in a plane normal to the substantially planar portion. In one embodiment, the flexing structures are flexure rings 115 with at least one flexure ring 115A positioned above a centrally located reservoir assembly controller board 125 and at least one flexure ring 115B positioned below the board 125. In a preferred embodiment, two flexure rings 115A are positioned above the centrally located reservoir assembly controller board 125 and two flexure rings 115B are positioned below the board 125. As can be seen in FIGS. 1A and 1B, the flexure rings 115A, 115B are separated from the reservoir assembly controller board 125 by an upper spacer 121 positioned above the board 125 and a lower spacer 122 positioned below the board 125. The flexure rings 115A, 115B are contained between the top ring clamp 110 and the upper spacer 121 above the reservoir assembly controller board 125 and between the bottom ring clamp 130 and the lower spacer 122 below the board 125. Also included is a center spacer 120 positioned in a center hole of the reservoir assembly controller board 125.

While FIGS. 1A and 1B depict the flexure assembly 100 as having only one ring shaped spacer 121 above and one spacer 122 below the reservoir assembly controller board 125, any number of spacing units can be used and the spacing units can be of different shapes, although circular or ring shapes are preferred. The spacing units are configured to fit the components of the flexure assembly correctly together. In one embodiment, the spacing units are composed of general purpose aluminum. In a preferred embodiment, the spacers are ring shaped with clearance holes in the center to ensure clearance of the flexure arms with the reservoir assembly controller board. In one embodiment, the upper spacer 121 has a thickness of 0.1 to 0.3 inches and the lower spacer 122 has a thickness that is less than the upper spacer and in a range of 0.05 to 0.2 inches.

In one embodiment, the flexure rings 115 have curved arms which allow for movement, particularly vertical movement, of the magnets within the flexure assembly 100 when the reservoir weight changes. Signals representative of the changes in the magnetic fields are processed by the reservoir assembly controller board 125 to yield weight measurements. The magnets are secured with an adhesive paste to the top center ring 105 and to bottom center ring 135 of the flexure assembly 100.

Figure 2:
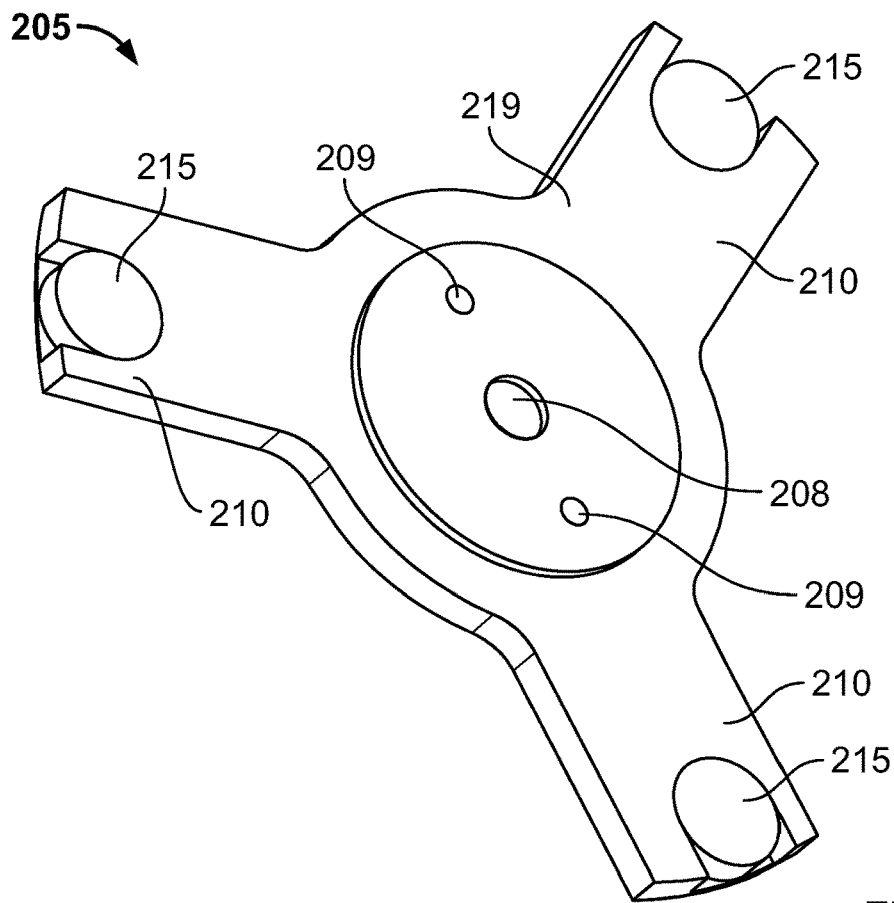
FIG. 2 is an illustration of one embodiment of a star shaped top center ring of the flexure assembly, depicting three spokes with a magnet placed in the end of each spoke.

FIG. 2 is an illustration of one embodiment of a star shaped top center ring 205 of the flexure assembly, depicting three spokes 210, each connected to a circular hub 219, with a magnet 215 placed, positioned, and/or embedded at the end of each spoke 210. Also depicted are the dowel pin holes 209 and the center screw hole 208. The magnets 215 are positioned 120° apart from one another at the end of each spoke 210.

Figure 3:
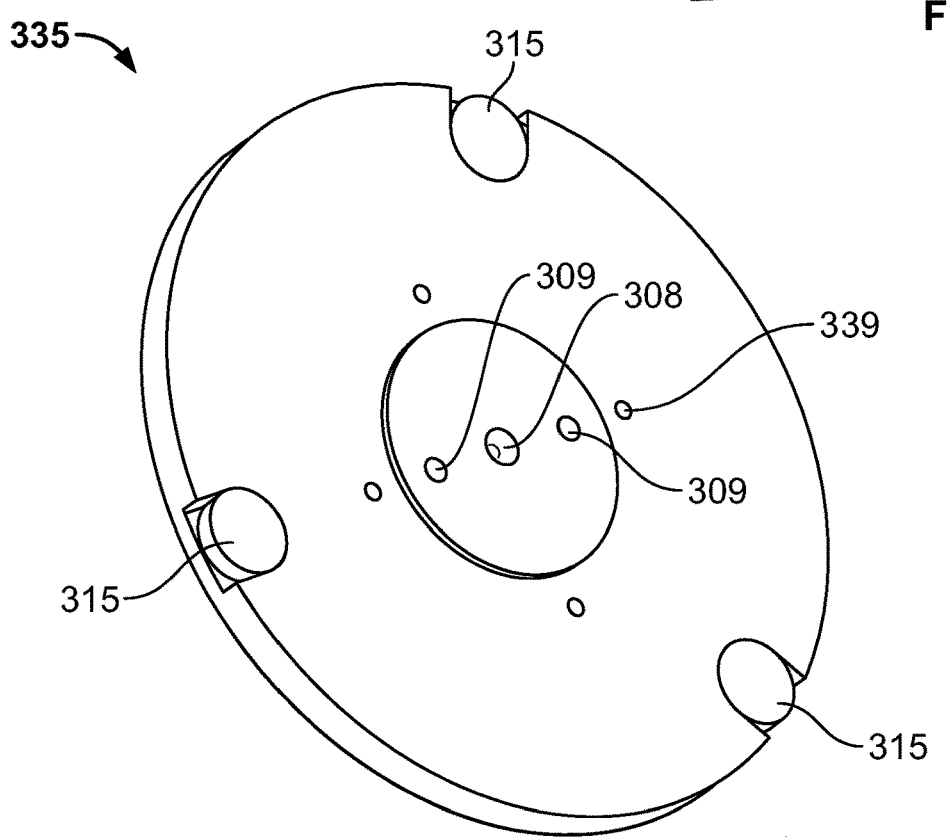
FIG. 3 is an illustration of one embodiment of a circular shaped lower tapped center ring of the flexure assembly, depicting three magnets placed in the periphery of the ring.

FIG. 3 is an illustration of one embodiment of a circular shaped bottom tapped center ring 335 of the flexure assembly, depicting three magnets 315 placed in the periphery of the ring 335. The magnets are also positioned 120 degrees relative to each other, as measured from the center of the bottom ring 335. Also visible are holes for receiving screws 339, dowel pins 309, and a center screw 308. The bottom center ring 335 transfers the load from the attached reservoir structure to the entire assembly. In other various embodiments, more or less than three magnets are used in the top center ring and bottom center ring as long as each ring contains the same number of magnets and the magnets are aligned in the same vertical axis.

In one embodiment, each magnet 215, 315 in the top center ring and in the bottom tapped center ring is a Neodymium (NdFeB) grade N42 disc magnet and measures 0.5 inches in diameter by 0.125 inches in thickness. In one embodiment, the magnets 215, 315 are heated for a predetermined period of time before assembly to process irreversible magnetic losses that naturally occur over time with heat. In one embodiment, the magnets are baked over 100 hours prior to assembly. Once the flexure assembly is fully assembled, the top center ring and bottom tapped center ring are positioned in relation to one another such that each magnet 215 of the top center ring is located directly above a corresponding magnet 315 of the bottom center ring. Preferably, in the fully assembled system, a constant distance or gap is established between each magnet 215 of the top center ring and each corresponding magnet 315 of the bottom center ring. In one embodiment, the constant gap is between 0.4 to 1.0, and more specifically approximately 0.7 inches, in the nominal plane.

Use of the flexure assembly disclosed herein results in a magnetic dampening of mechanical oscillations encountered in the prior art. In particular, the shape of the arms in conjunction with the placement of the magnets improves balance of the overall assembly by averaging out readings across the magnets. Magnet placement is also beneficial in averaging measurements during movement and with vibration of the system. In addition, as discussed below, the copper pours of the circuit board generate magnetic fields that dampen oscillations caused by eddy currents within the assembly.

FIG. 4 is an illustration of one embodiment of a flexure ring 400 of the flexure assembly. In one embodiment, each flexure ring 400 includes three folded beams or curved arms 405 which bend in the same plane and allow for displacement of the center of the ring 415 in the vertical plane as a weight is applied to the flexure assembly. Each arm 405 connects, on one end, to a generally triangular shaped hub 415 and, on the other end, to a circular outer ring 425. Each arm 405 preferably has a first linear portion 405A, with one end connected to the ring 425 and the other end culminating in a curved portion 405B. The curved portion 405B connects to a second linear portion 405C which, at its other end, culminates in a second curved portion 405D that attaches to the central hub 415. Each flexure ring includes a plurality of screw holes 410 in the circular outer ring through which screws pass to secure the flexure assembly components together. In other embodiments, varying flexure ring shapes can be used depending on the positioning and number of magnets. In one embodiment, the flexure rings 400 are made of aluminum 2024-T3 and do not comprise stainless steel, since stainless steel fails to prevent creep, or deformation of the material due to the application of force over time. Aluminum 2024-T3 provides a high yield strength of 50,000-55,000 PSI and a modulus of elasticity of approximately 10,600,000 PSI. In one embodiment, the flexure assembly is capable of calculating weight measurements up to 25 KG. In one embodiment, the operating weight of the reservoir contents is between 17 and 18 KG.

FIG. 4B depicts the minimum 450 and maximum 455 points of stress on a flexure ring 400 with an 18 KG load in accordance with one embodiment of the present specification. In one embodiment, using a parallel configuration of two sets of two adjacent flexure rings, each comprised of aluminum 2024-T3 and configured as depicted in FIG. 4B, a center load of 18 KG produces a minimum stress of 0.0 PSI at point 450 and a maximum stress of 37,860.0 PSI, or approximately 37,600 PSI, at point 455. The maximum stress point 455 is at the position of the first u-shaped bend in each arm, as seen when moving inwardly from the periphery of each ring. The minimum stress point 450 is positioned on the periphery of the ring. Measurable stress is seen at the point of attachment between the first linear portion 405A and the ring 425, the first curved portion 405B, and the second curved portion 405D in each of the flexure arms.

FIG. 4C depicts the minimum 460 and maximum 465 points of strain on a flexure ring 400 with an 18 KG load in accordance with one embodiment of the present specification. In one embodiment, using a parallel configuration of two sets of two adjacent flexure rings, each comprised of aluminum 2024-T3 and configured as depicted in FIG. 4C, a center load of 18 KG produces a minimum strain of 1.290e-018 at point 460 and a maximum strain of approximately 2.620e-003, or approximately 0.0026 IN/IN at point 465. The maximum strain point 465 is at the position of the first curved bend in each arm, as seen when moving inwardly from the periphery of each ring. The minimum strain point 460 is positioned on the periphery of the ring. Measurable stress is seen at the point of attachment between the first linear portion 405A and the ring 425, the first curved portion 405B, and the second curved portion 405D in each of the flexure arms.

Figure 4D:
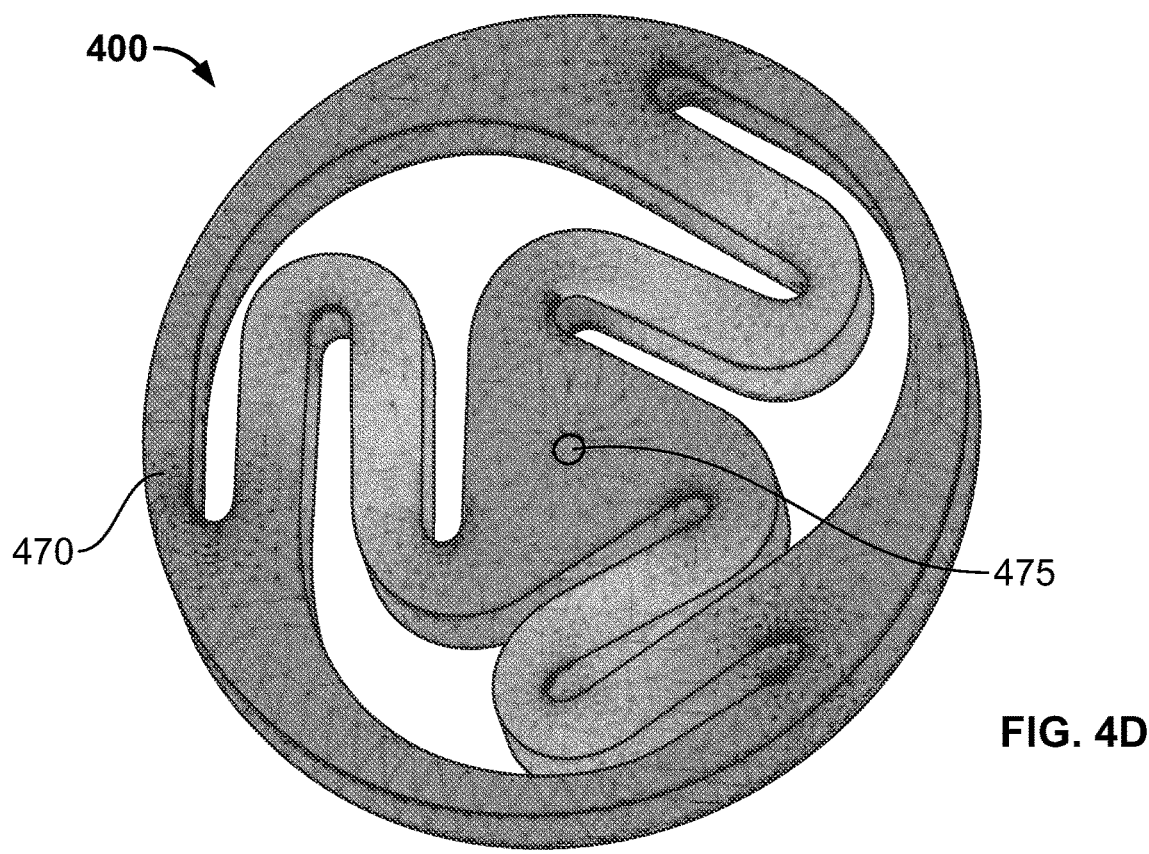
FIG. 4D is an illustration depicting the minimum and maximum points of displacement on a flexure ring with an 18 KG load in accordance with one embodiment of the present specification.

FIG. 4D depicts the minimum 470 and maximum 475 points of displacement on a flexure ring 400 with an 18 KG load in accordance with one embodiment of the present specification. In one embodiment, using a parallel configuration of two sets of two adjacent flexure rings, each comprised of aluminum 2024-T3 and configured as depicted in FIG. 4D, a center load of 18 KG produces a minimum displacement of 3.937e-032 at point 470 and a maximum displacement of approximately 1.581e-001, or approximately 0.158 IN at point 475. The maximum displacement point 475 is at the center of each ring. The minimum displacement point 470 is positioned on the periphery of the ring. In one embodiment, when in use with a load of approximately 17 KG, the rings exhibit a displacement of approximately 0.130 IN.

In one embodiment, the flexure rings exhibit a maximum stress of 37,000 PSI, a maximum strain at maximum stress of 0.0026 IN/IN, and a maximum displacement at the triangular shaped central hub of 0.158 inches. In a preferred embodiment, the flexure assembly comprises a set of flexure rings above the reservoir assembly controller board and a set below the board, with each set having two flexure rings stacked one directly atop the other. The shape of the flexure rings as depicted in FIGS. 4A through 4D is ideal for equally distributing and minimizing the stress and strain among the arms while allowing for the greatest displacement at the center, thereby providing more accurate weight measurements. In addition, using a plurality of flexure rings lessens the occurrence of creep. Minimizing creep improves the longevity of the flexure assembly.

Figure 5:
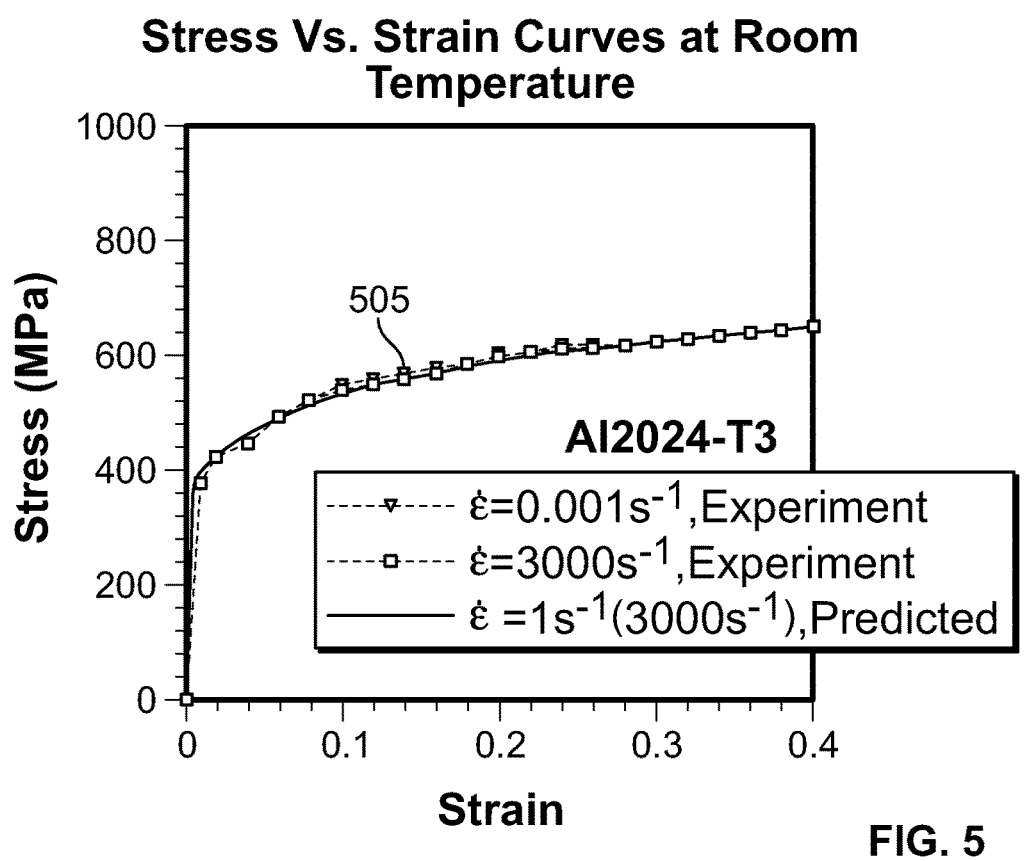
FIG. 5 is a graph displaying stress versus strain curves for aluminum 2024-T3 at room temperature.

FIG. 5 is a graph displaying stress versus strain curves for aluminum 2024-T3 at room temperature. As can be seen by the predicted and experimental result curves 505, the strain increases exponentially up to a stress of 400 megapascal (MPa) and then begins to level out as the stress approaches 600 MPa. The linearity of the curve as the stress increases over 400 MPa signifies that the aluminum 2024-T3 exhibits little increase in strain in response to high stress, thus making it an ideal material for resisting creep.

The blades or arms of the flexure rings are arranged in parallel to minimize out of plane moments of the flexure assembly. In various embodiments, each flexure ring has a thickness in the range of 0.01 to 0.1 inches. In one embodiment, each flexure ring has a thickness of 0.05 inches. The center spacer, top center ring, and bottom center ring are connected to the triangular shaped central hub by the two dowel pins such that the components of the assembly containing the magnets move while the reservoir assembly controller board is fixed.

Figure 6A:
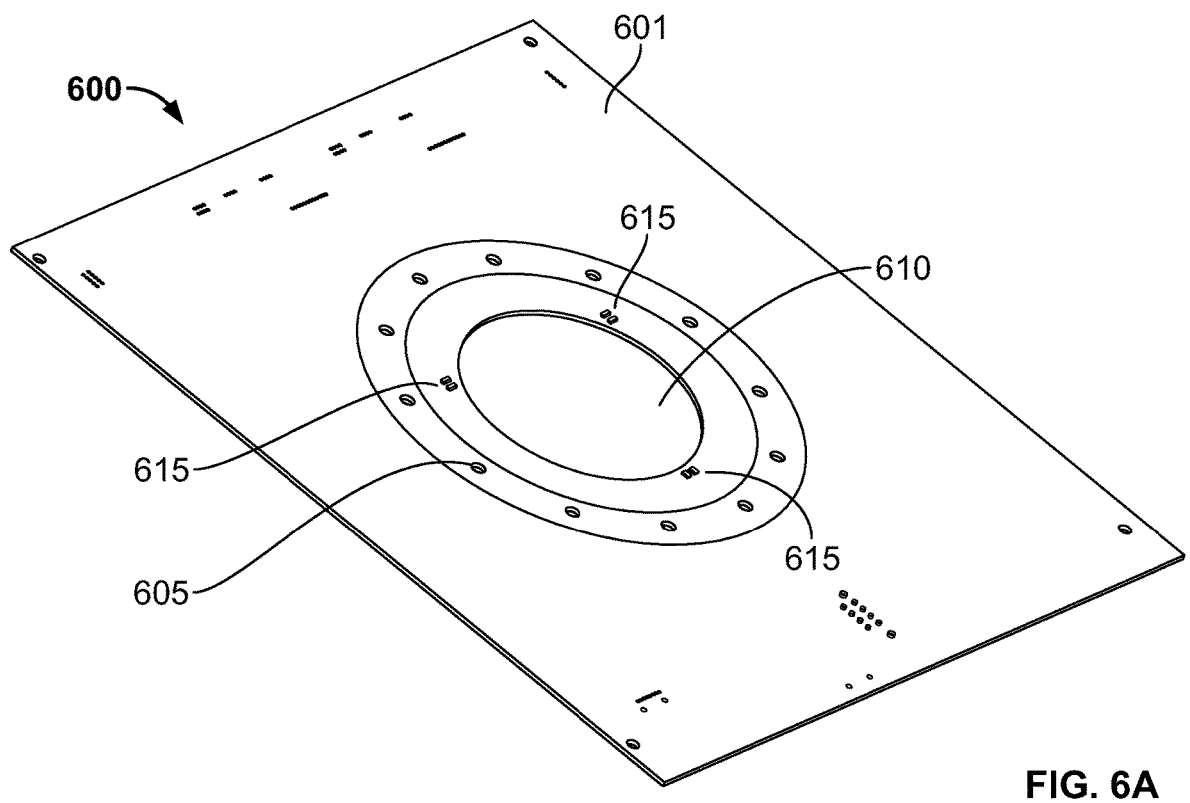
FIG. 6A is an illustration of one embodiment of the reservoir assembly controller board of the flexure assembly, depicting the bottom surface of the board.
Figure 6B:
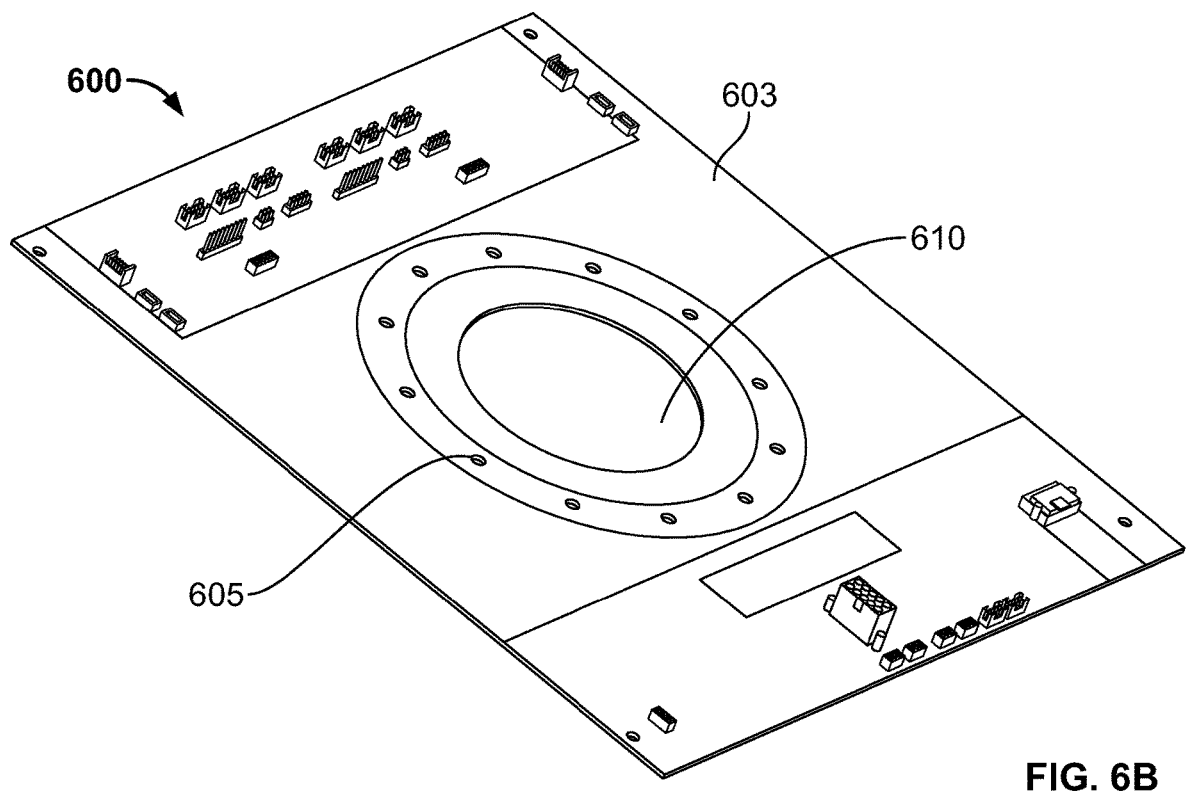
FIG. 6B is an illustration of the embodiment of the reservoir assembly controller board of the flexure assembly of FIG. 6A, depicting the top surface of the board.

FIGS. 6A and 6B are illustrations of one embodiment of the reservoir assembly controller board 600 of the flexure assembly, depicting the bottom 601 and top 603 surfaces respectively, of the board. Referring to both FIGS. 6A and 6B, the reservoir assembly controller board 600 includes a circular opening 610 at its center that receives a center spacer once the flexure assembly is fully assembled. The board 600 also includes a plurality of screw holes 605 along a circular path circumscribing the center circular opening 610. Screws pass through these holes 605 to secure the components of the flexure assembly together. Referring to FIG. 6A, the bottom surface 601 of the reservoir assembly controller board 600 includes three pairs of hall sensors 615. In various embodiments, more or less than three hall sensor pairs are used depending on the number of magnets included in the assembly. The hall sensor pairs 615 are offset from the magnetic center of axis of the magnets included in the top center ring and bottom center ring. The hall sensor pairs 615 are positioned 120° apart from one another to compensate for reservoir pan center of gravity imbalances. In one embodiment, the hall sensor pairs 615 have a sensitivity of 1.3 mV/gauss.

In one embodiment, the reservoir assembly controller board measures 11 inches wide by 12 inches deep and includes air temperature sensors spaced apart from one another by 120°. In one embodiment, the reservoir assembly controller board further includes an eddy current dampener, created by magnetic fields generated in the copper pours of the board, for dampening vibration. The magnetic fields generated by the copper pours of the board effectively encircle the flexure assembly. As the magnets move and the magnetic field changes, an eddy current is generated which can produce oscillations and thereby errors in weight measurement. The copper pours of the circuit board generate magnetic fields which eliminate the oscillations by removing or dampening the eddy current.

Figure 7:
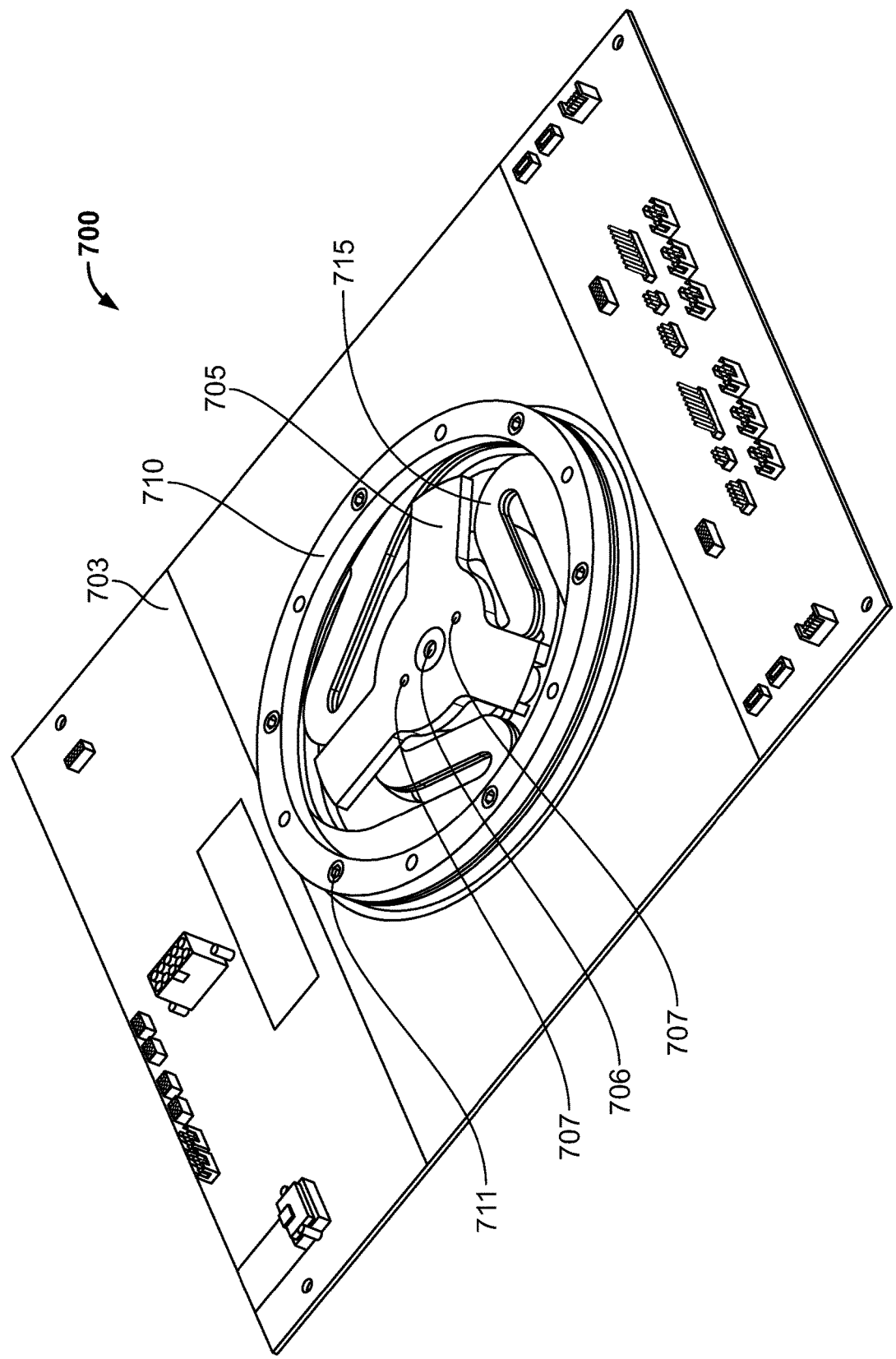
FIG. 7 is a top down view illustration of one embodiment of a fully assembled flexure assembly.

FIG. 7 is a top down view illustration of one embodiment of a fully assembled flexure assembly 700. The top surface of the reservoir assembly controller board 703, top ring clamp 710, top center ring 705, and uppermost flexure ring 715 are visible in this view. Also depicted are six peripheral screws 711, one center screw 706, and two dowel pins 707 securing the flexure assembly 700 together.

Figure 8:
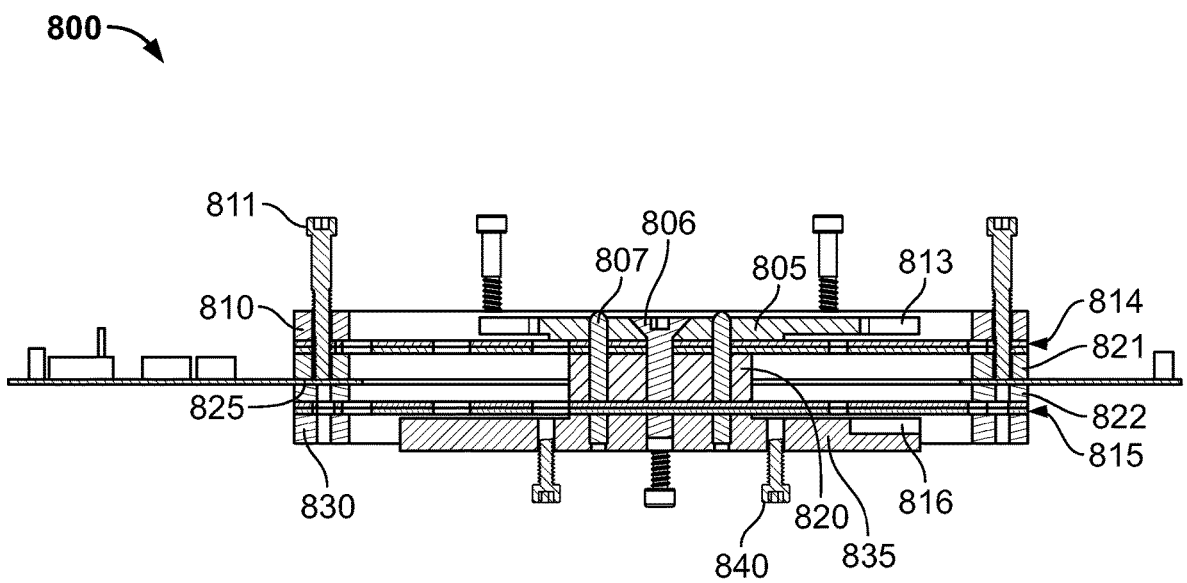
FIG. 8 is a cross-sectional side view illustration of one embodiment of a fully assembled flexure assembly.

FIG. 8 is a cross-sectional side view illustration of one embodiment of a fully assembled flexure assembly 800. Positioned above the reservoir assembly controller board 825 are the top center ring 805, top ring clamp 810, one of the plurality of upper magnets 813, an upper flexure ring set 814, and the upper spacer 821. The center spacer 820 is positioned in the center opening of the reservoir assembly controller board 825. Positioned below the reservoir assembly controller board are the lower spacer 822, a lower flexure ring set 815, one of the plurality of lower magnets 816, the bottom tapped ring clamp 830, and the bottom center ring 835. Passing into and through the assembly 800 from the top and at the periphery are six securing screws 811. A center screw 806 passes into and through the assembly 800, including the center spacer 820, at the center of the assembly 800. Two dowel pins 807 also pass into and through the assembly 800 at its center. For securing the second internal frame to the flexure assembly 800, four screws 840 pass through a center member of the second internal frame (not shown) and into the bottom center ring 835.

Figure 9:
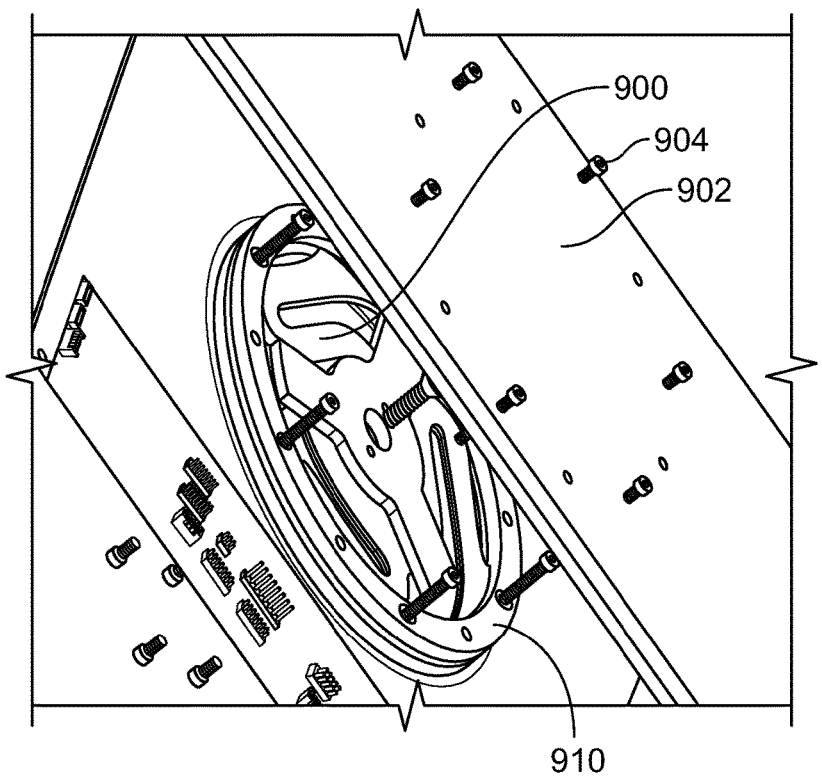
FIG. 9 is an oblique top down view illustration of one embodiment of a fully assembled flexure assembly and a scale support of the dialysis machine.
Figure 10:
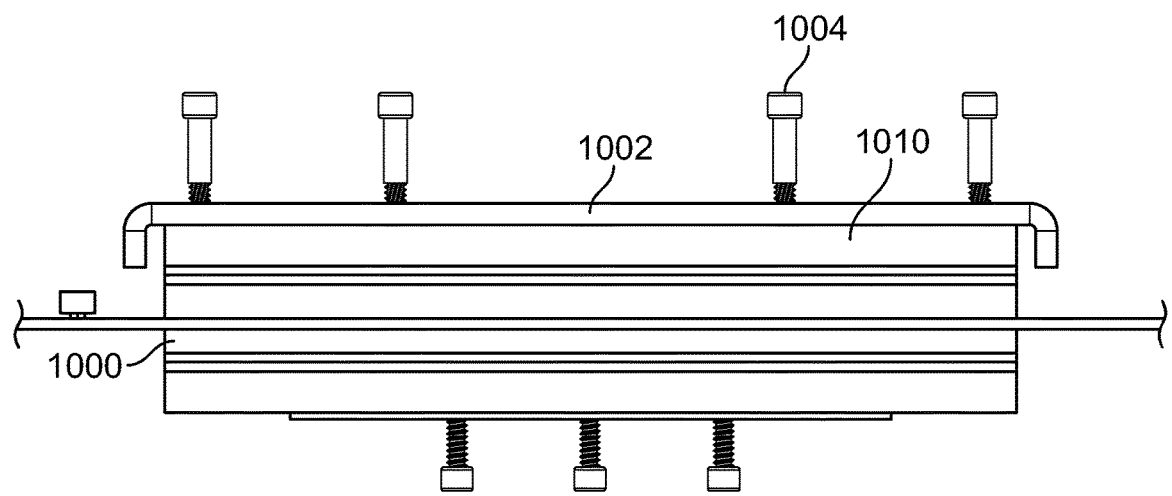
FIG. 10 is a cross-sectional side view illustration of the embodiment of a fully assembled flexure assembly and scale support of FIG. 9.

FIG. 9 is an oblique top down view illustration of one embodiment of a fully assembled flexure assembly 900 and a scale support 902 of the dialysis machine. Screws 904 pass through the top of the scale support 902 and into holes in the top ring clamp 910 of the flexure assembly 900. FIG. 10 is a cross-sectional side view illustration of the embodiment of a fully assembled flexure assembly 1000 and scale support 1002 of FIG. 9. The screws 1004 pass through the top of the scale support 1002 and into the top ring clamp 1010, securing the flexure assembly 1000 to the scale support 1002, which is preferably integral with the primary frame defining the dialysis machine housing.

Figure 11:
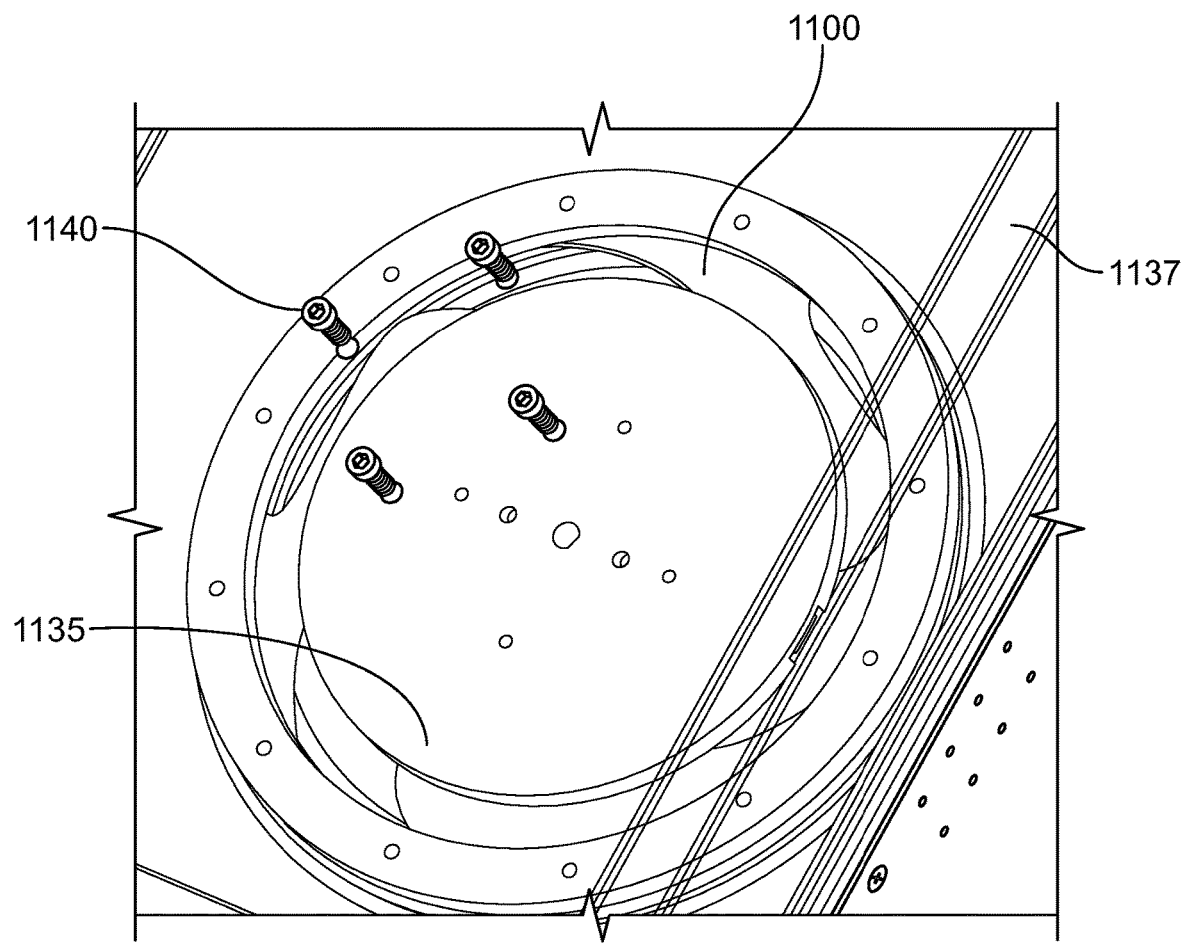
FIG. 11 is an oblique bottom up view illustration of one embodiment of a fully assembled flexure assembly and a pan hanger of the dialysis machine.
Figure 12:
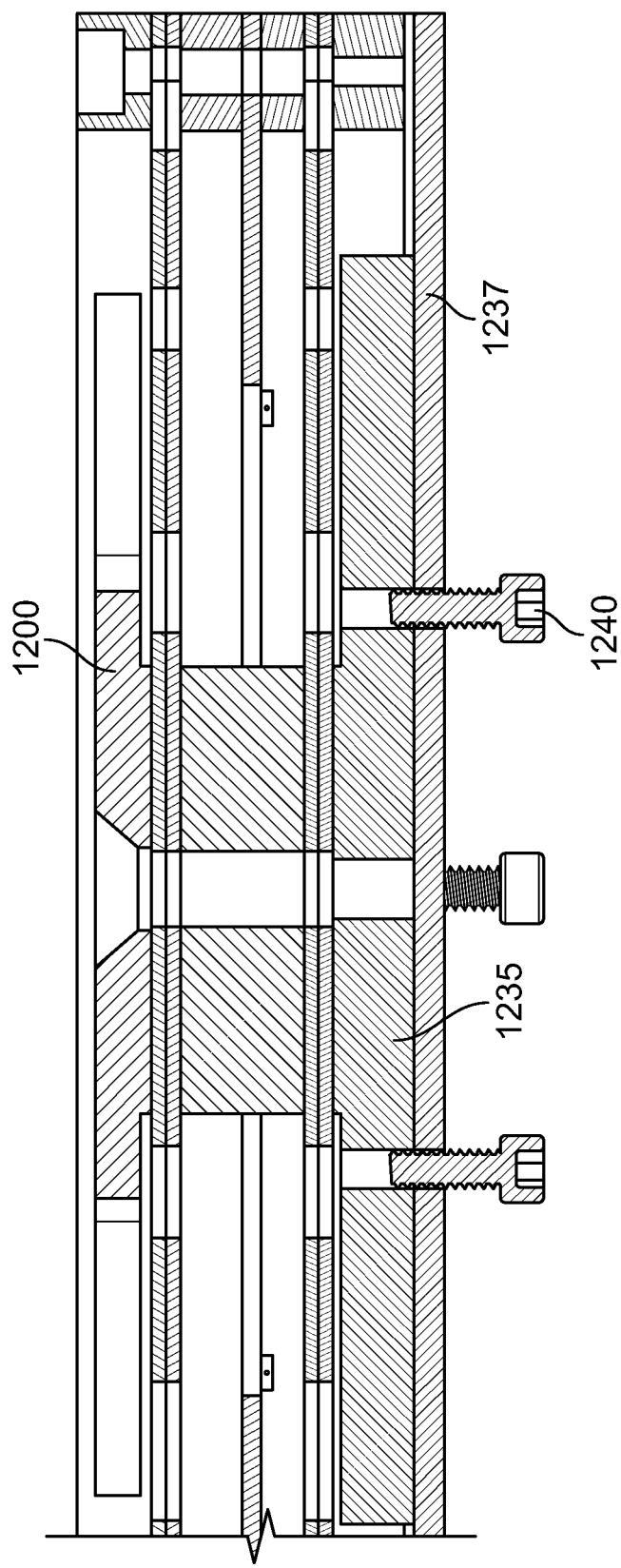
FIG. 12 is a cross-sectional side view illustration of the embodiment of a fully assembled flexure assembly and pan hanger of FIG. 11.

FIG. 11 is an oblique bottom up view illustration of one embodiment of a fully assembled flexure assembly 1100 and a pan hanger 1137 of the dialysis machine. Screws 1140 pass upward through the pan hanger 1137 and into the bottom tapped center ring 1135 of the flexure assembly 1100. FIG. 12 is a cross-sectional side view illustration of the embodiment of a fully assembled flexure assembly 1200 and pan hanger 1237 of FIG. 11. The screws 1240 pass through the bottom of the pan hanger 1237 and into the bottom tapped center ring 1235, securing the flexure assembly 1200 to the pan or reservoir hanger 1237.

FIGS. 13A and 13B are front and side view illustrations, respectively, of one embodiment of a dialysis machine, depicting the flexure assembly disclosed herein 1312 and first 1360 and second 1365 internal frames therein. The front and sides of the dialysis machine have been made transparent and the reservoir unit has been removed to enhance visualization. The dialysis machine comprises top 1301 and bottom 1303 sections. In one embodiment, the bottom section 1303 houses the flexure assembly 1312 and associated components. The second internal frame 1365 is attached to the bottom surface of a top portion of a frame that defines the housing of the bottom section 1303 of the dialysis machine. The second internal frame 1365 includes a top plate, two side walls with openings 1366 for passage of the top plate of the first internal frame 1360, and a pair of horizontal tracks 1348. In one embodiment, the horizontal tracks 1348 of the second internal frame 1365 extend along the front to back axis of the dialysis machine, from a point proximate the front of the machine to a point proximate the back of the machine.

The flexure assembly disclosed herein 1312 is attached to the bottom surface of a top portion of a frame that defines the housing of the bottom section 1303 of the dialysis machine. In one embodiment, a top plate of the first internal frame 1360 connects to the bottom of the flexure assembly 1312. The first internal frame includes a top plate, two sides with horizontal tracks 1345, and a back plate 1332 with electrical contact elements 1333. In one embodiment, the horizontal tracks 1345 of the first internal frame 1360 extend along the front to back axis of the dialysis machine, from a point proximate the front of the machine to a point proximate the back of the machine. In one embodiment, the back plate 1332 is rectangular shaped and includes the electrical contact elements 1333 which align with and contact the electrical contact plate on the insertion side of the reservoir unit. The first internal frame 1360 includes a pair of tracks 1345, with one track extending along each side of the dialysis machine. Each track 1345 is connected to the back plate 1332 at its back end. When inserted, the reservoir unit is suspended on the tracks 1345 of the first internal frame 1360.

The three hall sensor pairs of the flexure assembly are fixed in a static magnetic field. When the assembly is used to measure the contents of the reservoir, the magnetic field moves in the vertical axis and this movement is used to calculate the weight of the reservoir contents. Before a weight is applied, the assembly is calibrated with a voltage output of zero. The magnetic fields of the upper and lower magnets repel each other and create a centerline zero magnetic plane. The pole orientation of the magnets insures an increasing voltage output as a weight is applied and the magnets move in relation to the hall sensors. A processor on the circuit board translates the change in voltage into a weight measurement using a function of the voltage. It should be appreciated that the weight is a function of voltage changes and can be experimentally derived by plotting different weights against different voltage levels and/or voltage changes. That experimentally derived plotting will yield an implementable function that relates a measured voltage level or measured voltage change against weight values, thereby allowing a processor to accurately calculate a weight from an inputted voltage level or voltage change.

In one embodiment, the hall sensors output an analog signal proportional to the change in voltage. The output is converted by an analog to digital converter (ADC) into a digital output to obtain a higher resolution. In one embodiment, the weight, in grams, of the contents of the reservoir unit is calculated using the following equation:

$$\text{Weight} = w_3 + w_2 + w_1 + w_0 \quad [\text{EQUATION 1}]$$

wherein, $w_0 = k_0$;
$w_1 = k_1 * \text{ADC}$ value (in milliVolts) of the hall sensor (Hall);
$w_2 = k_2 * \text{ADC}$ voltage reference (Vref) value; and,
$w_3 = k_3 * \text{ADC(Hall)} * \text{ADC(Vref)}$ $k_0$ through $k_3$ represent constants and, in various embodiments, have the following values: $k_0 = -7925.4 +/- 0.10$; $k_1 = 328.741\text{e-}3 +/- 1.0\text{e-}6$; $k_2 = -73.688\text{e-}3 +/- 1.0\text{e-}6$; and, $k_3 = 935.35\text{e-}9 +/- 10\text{e-}12$.

Figure 14A:
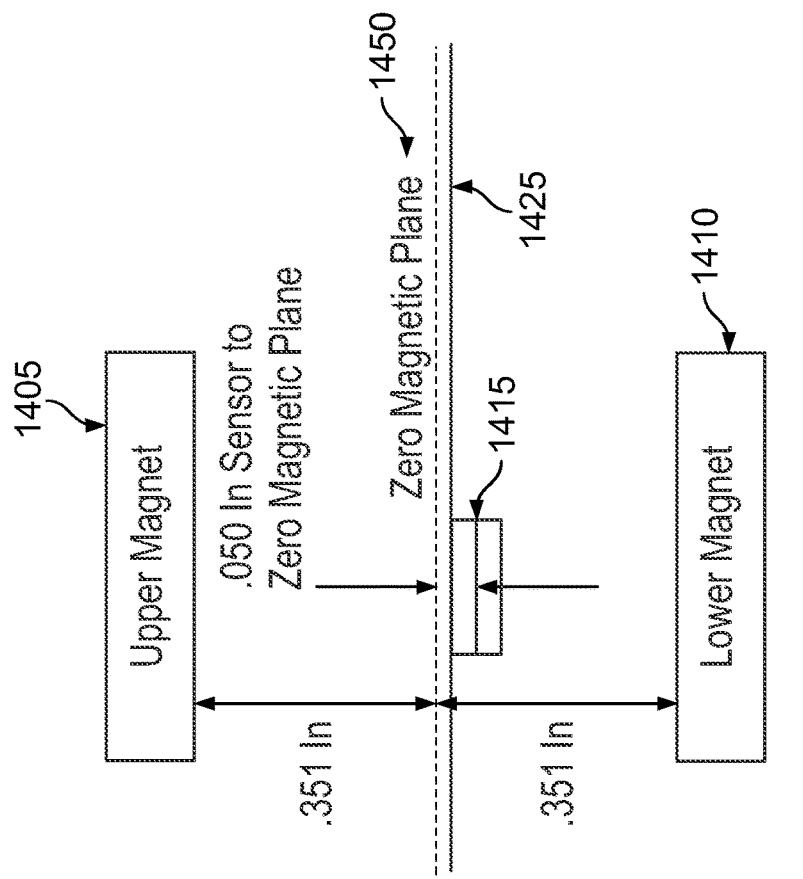
FIG. 14A is a block diagram of one embodiment of the magnets and hall sensor of the flexure assembly, depicting the relative position of the zero magnetic plane when the assembly is unloaded.

FIG. 14A is a block diagram of one embodiment of the magnets 1405, 1410 and hall sensor 1415 of the flexure assembly, depicting the relative position of the zero magnetic plane 1450 when the assembly is not bearing a load. Both the upper magnet 1405 and the lower magnet 1410 maintain a constant distance, e.g. a specific amount in a range of 0.1 to 0.5 inches, from a center point between the two, establishing a constant zero magnetic plane 1450. With no pan loaded, the hall sensor 1415 on the reservoir assembly controller board 1425 has a predefined clearance, such as a specific amount in a range of 0.1 to 0.3 inches, from its bottom surface to the lower magnet 1410 and is positioned a predefined distance, such as 0.05 to 0.25 inches, below the zero magnetic plane 1450.

Figure 14B:
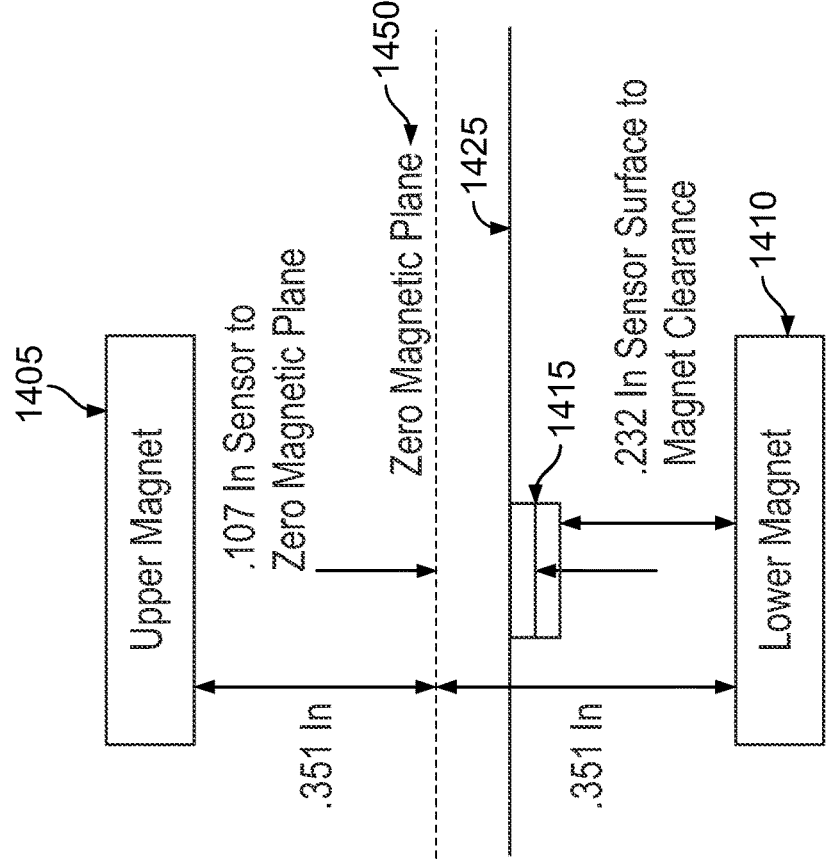
FIG. 14B is a block diagram of one embodiment of the magnets and Hall sensor of the flexure assembly, depicting the relative position of the zero magnetic plane when the assembly is loaded with an empty reservoir pan.

FIG. 14B is a block diagram of one embodiment of the magnets 1405, 1410 and hall sensor 1415 of the flexure assembly, depicting the relative position of the zero magnetic plane 1450 when the assembly is loaded with an empty reservoir pan. The applied load with an empty pan is approximately 7 kg and is the tare weight. Both the upper magnet 1405 and the lower magnet 1410 maintain the same constant distance, as discussed above, from a center point between the two, establishing a constant zero magnetic plane 1450. With an empty pan loaded, the hall sensor 1415 on the reservoir assembly controller board 1425 has a different position, one which is closer to the zero magnetic plane 1450. For example, before any load, the distance from the hall sensor 1415 to the zero magnetic plane 1450 is 0.107 inches and decreases to 0.05 inches when an empty pan is loaded onto the assembly.

Figure 14D:
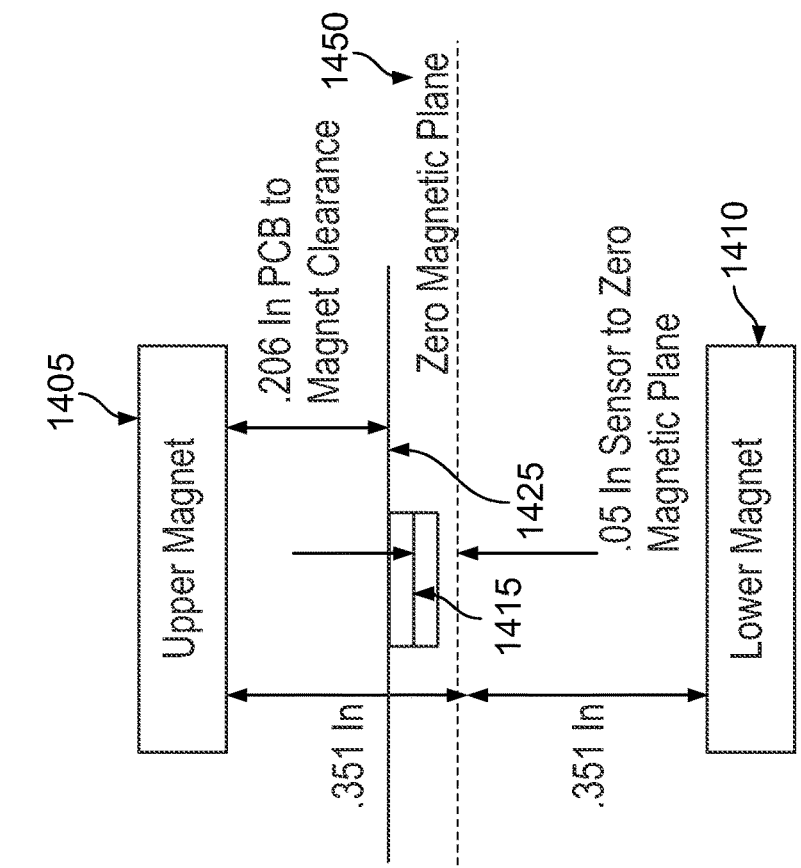
FIG. 14C is a block diagram of one embodiment of the magnets and hall sensor of the flexure assembly, depicting the relative position of the zero magnetic plane when the assembly is loaded with a half full reservoir pan; and, FIG. 14D is a block diagram of one embodiment of the magnets and hall sensor of the flexure assembly, depicting the relative position of the zero magnetic plane when the assembly is loaded with a full reservoir pan.
Figure 14C:
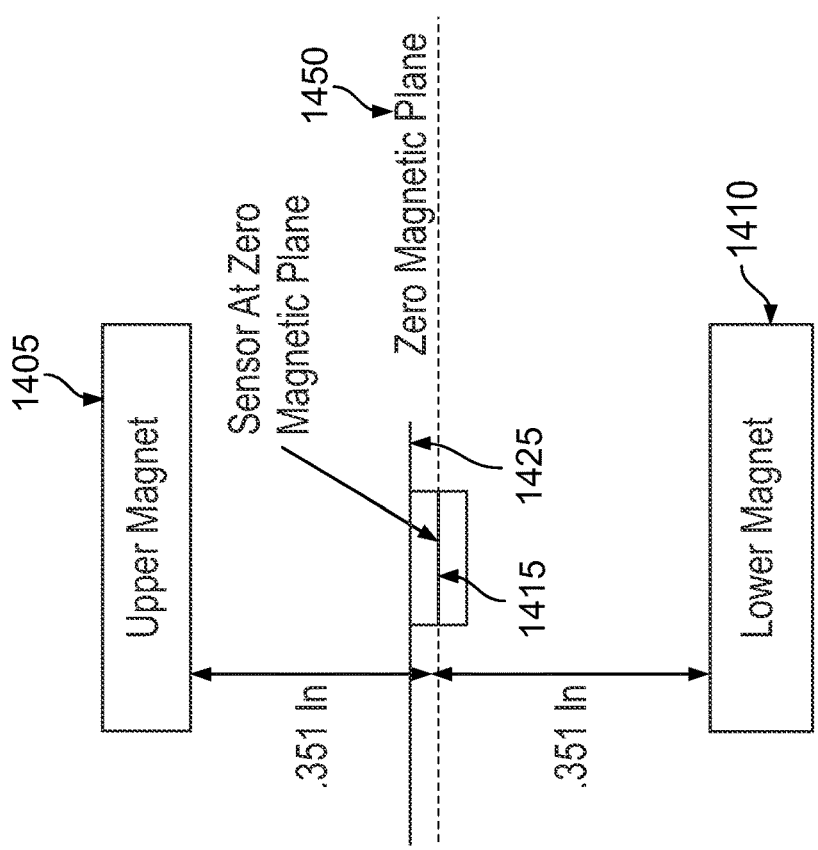

FIG. 14C is a block diagram of one embodiment of the magnets 1405, 1410 and hall sensor 1415 of the flexure assembly, depicting the relative position of the zero magnetic plane 1450 when the assembly is loaded with a half full reservoir pan. The applied load with a half full pan is approximately 12.5 kg. Both the upper magnet 1405 and the lower magnet 1410 maintain the same constant distance described above from a center point between the two, establishing a constant zero magnetic plane 1450. With a half full pan loaded, the hall sensor 1415 on the reservoir assembly controller board 1425 is positioned almost directly on the zero magnetic plane 1450.

FIG. 14D is a block diagram of one embodiment of the magnets 1405, 1410 and hall sensor 1415 of the flexure assembly, depicting the relative position of the zero magnetic plane 1450 when the assembly is loaded with a full reservoir pan. The applied load of a full pan is approximately 18 kg. Both the upper magnet 1405 and the lower magnet 1410 maintain the same constant distance described above from a center point between the two, establishing a constant zero magnetic plane 1450. With a full pan loaded, the reservoir assembly controller board 1425 has a clearance of 0.206 inches from its top surface to the upper magnet 1405 and the hall sensor 1415 is positioned 0.05 inches above the zero magnetic plane 1450.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:
1. A dialysis machine comprising:
a dialyzer configured to receive blood from a patient;

a first frame defined by a top plate, a first side plate connected to the top plate, and a second side plate connected to the top plate;
a first track attached to the first side plate;
a second track positioned parallel to the first track and attached to the second side plate;
a reservoir configured to be slidably received onto the first track and the second track and configured to be in fluid communication with the dialyzer;
a second frame separate from the first frame; and
a suspension assembly configured to connect the first frame to the second frame.

2. The dialysis machine of claim 1, further comprising a back plate connected to the top plate, wherein the back plate further comprises a first plurality of electrical contacts.

3. The dialysis machine of claim 2, wherein the reservoir comprises a second plurality of electrical contacts configured to interface with the first plurality of electrical contacts upon being slidably received onto the first track and the second track.

4. The dialysis machine of claim 1, wherein the suspension assembly comprises a plurality of flexing structures configured to dampen a mechanical oscillation of the first frame relative to the second frame.

5. The dialysis machine of claim 1, wherein the first track and second track are configured to extend from a point proximate a front of the dialysis machine to a point proximate a back of the dialysis machine.

6. The dialysis machine of claim 1, wherein the suspension assembly comprises a circuit board configured to translate a change in voltage into data indicative of a weight measurement.

7. The dialysis machine of claim 6, wherein, within the suspension assembly, the circuit board is positioned between a top flexing structure and a bottom flexing structure of the plurality of flexing structures positioned above and below the circuit board.

8. The dialysis machine of claim 1, wherein the second frame defines a central frame around which a housing of the dialysis machine is positioned.

9. A dialysis machine comprising:
a dialyzer configured to receive blood from a patient;
a first frame defined by a top plate, a first side plate connected to the top plate, a second side plate connected to the top plate, and a back plate connected to the top plate, wherein the back plate further comprises a first plurality of electrical contacts;
a first track attached to the first side plate;
a second track positioned parallel to the first track and attached to the second side plate;
a reservoir configured to be slidably received onto the first track and the second track and configured to be in fluid communication with the dialyzer, wherein the reservoir comprises a second plurality of electrical contacts configured to interface with the first plurality of electrical contacts upon being slidably received onto the first track and the second track;
a second frame separate from the first frame; and
a suspension assembly configured to connect the first frame to the second frame, wherein the suspension assembly comprises a plurality of flexing structures configured to dampen a mechanical oscillation of the first frame relative to the second frame.

10. The dialysis machine of claim 9, wherein the suspension assembly comprises a circuit board configured to translate a change in voltage into data indicative of a weight measurement.

11. The dialysis machine of claim 10, wherein, within the suspension assembly, the circuit board is positioned between a top flexing structure and a bottom flexing structure of the plurality of flexing structures positioned above and below the circuit board.

12. The dialysis machine of claim 11, wherein the second frame defines a central frame around which a housing of the dialysis machine is positioned.

13. A method of installing a reservoir into a dialysis system, the method comprising:
providing a dialysis machine comprising:
a dialyzer configured to receive blood from a patient;
a first frame defined by a top plate, a first side plate connected to the top plate, and a second side plate connected to the top plate;
a first track attached to the first side plate;
a second track positioned parallel to the first track and attached to the second side plate;
a reservoir configured to be slidably received onto the first track and the second track and configured to be in fluid communication with the dialyzer;
a second frame separate from the first frame; and
a suspension assembly configured to connect the first frame to the second frame; and
sliding the reservoir onto the first track and the second track.

14. The method of claim 13, wherein the dialysis machine further comprises a back plate connected to the top plate, wherein the back plate further comprises a first plurality of electrical contacts.

15. The method of claim 14, wherein the reservoir comprises a second plurality of electrical contacts configured to interface with the first plurality of electrical contacts upon being slidably received onto the first track and the second track.

16. The method of claim 13, wherein the suspension assembly comprises a plurality of flexing structures configured to dampen a mechanical oscillation of the first frame relative to the second frame.

17. The method of claim 13, wherein the first track and second track are configured to extend from a point proximate a front of the dialysis machine to a point proximate a back of the dialysis machine.

18. The method of claim 13, wherein the suspension assembly comprises a circuit board configured to translate a change in voltage into data indicative of a weight measurement.

19. The method of claim 18, wherein, within the suspension assembly, the circuit board is positioned between a top flexing structure and a bottom flexing structure of the plurality of flexing structures positioned above and below the circuit board.

20. The method of claim 13, wherein the second frame defines a central frame around which a housing of the dialysis machine is positioned.

* * * * *